United States Patent
Khan et al.

(10) Patent No.: US 12,220,174 B2
(45) Date of Patent: Feb. 11, 2025

(54) IMPLANT FIT ANALYSIS

(71) Applicant: Australian Institute of Robotic Orthopaedics PTY LTD, Nedlands (AU)

(72) Inventors: Riaz Jan Kjell Khan, Cottesloe (AU); Daniel Paul Fick, Cottesloe (AU); William Brett Robertson, North Fremantle (AU); Richard Chipper, Mount Claremont (AU); Joshua Goncalves, Atwell (AU)

(73) Assignee: Australian Institute of Robotic Orthopaedics PTY LTD, Nedlands (AU)

( * ) Notice: Subject to any disclaimer, the term of this patent is extended or adjusted under 35 U.S.C. 154(b) by 778 days.

(21) Appl. No.: 17/255,783

(22) PCT Filed: Jun. 26, 2019

(86) PCT No.: PCT/AU2019/050664
§ 371 (c)(1),
(2) Date: Dec. 23, 2020

(87) PCT Pub. No.: WO2020/000038
PCT Pub. Date: Jan. 2, 2020

(65) Prior Publication Data
US 2021/0128247 A1 May 6, 2021

(30) Foreign Application Priority Data

Jun. 26, 2018 (AU) ................ 2018902290

(51) Int. Cl.
*A61B 34/10* (2016.01)
*A61F 2/32* (2006.01)
(Continued)

(52) U.S. Cl.
CPC ............... *A61B 34/10* (2016.02); *A61F 2/32* (2013.01); *A61F 2/38* (2013.01); *A61F 2/46* (2013.01);
(Continued)

(58) Field of Classification Search
CPC .. A61B 34/10; A61B 2034/102; G16H 20/40; G16H 50/20; A61F 2/32; A61F 2/38; A61F 2/46; A61F 2002/4633
See application file for complete search history.

(56) References Cited

U.S. PATENT DOCUMENTS

| 2004/0243148 A1 | 12/2004 | Wasielewski |
| 2008/0108912 A1 | 5/2008 | Node-Langlois |

(Continued)

FOREIGN PATENT DOCUMENTS

EP   2083758 A2   8/2009

OTHER PUBLICATIONS

International Search Report in related application No. PCT/AU2019/050664 dated Aug. 30, 2019.

*Primary Examiner* — Paul B Prebilic
(74) *Attorney, Agent, or Firm* — Kilpatrick Townsend & Stockton LLP

(57) ABSTRACT

Systems and methods for intraoperative implant fit analysis and longevity prediction for a prosthetic implant to be integrated with the physiological tissue of a patient, the method comprising the steps of: collection of data via a plurality of sensors situated in proximity to the tissue and implant and a plurality of data sources; determining tissue and implant state and morphology based on the collected data; generating compatibility information between the tissue and implant based on the determined tissue and implant state and morphology; processing compatibility information into a form adapted for evaluation against a pre-determined (Continued)

comparator; generating a means of predicting postoperative implant performance and longevity utilising the historical dataset of comparison information and postoperative results; and generating and providing corrective information for alteration of the tissue state and morphology for improved postoperative implant performance and longevity.

41 Claims, 14 Drawing Sheets

(51) Int. Cl.
    *A61F 2/38*     (2006.01)
    *A61F 2/46*     (2006.01)
    *G16H 20/40*     (2018.01)
    *G16H 50/20*     (2018.01)

(52) U.S. Cl.
    CPC ............ *G16H 20/40* (2018.01); *G16H 50/20* (2018.01); *A61B 2034/102* (2016.02); *A61F 2002/4633* (2013.01)

(56) References Cited

U.S. PATENT DOCUMENTS

| | | |
|---|---|---|
| 2009/0264894 A1 | 10/2009 | Wasielewski |
| 2011/0218543 A1 | 9/2011 | van der Walt |
| 2011/0251835 A1* | 10/2011 | Amiot ................. A61B 34/20 703/2 |
| 2011/0257653 A1* | 10/2011 | Hughes ................. A61B 34/20 606/86 R |
| 2012/0271599 A1* | 10/2012 | Lavallee ............... A61B 34/20 703/1 |
| 2012/0323247 A1 | 12/2012 | Bettenga |
| 2013/0253379 A1* | 9/2013 | Mahfouz ............... G16H 40/63 600/595 |
| 2014/0135773 A1* | 5/2014 | Stein ..................... A61B 34/20 606/100 |
| 2014/0244220 A1* | 8/2014 | McKinnon ............ A61F 2/02 703/1 |
| 2015/0106024 A1 | 4/2015 | Lightcap et al. |
| 2015/0193590 A1 | 7/2015 | Miles et al. |
| 2015/0297362 A1* | 10/2015 | Singh ................... A61F 2/3609 623/22.15 |
| 2018/0303552 A1 | 10/2018 | Ryan et al. |
| 2019/0209242 A1* | 7/2019 | Padrick ................. G06N 20/20 |
| 2021/0128247 A1* | 5/2021 | Khan .................... G16H 10/60 |
| 2022/0068496 A1* | 3/2022 | Khan .................... A61B 5/1032 |
| 2024/0206990 A1* | 6/2024 | Boddington ......... G06V 10/426 |

* cited by examiner

IMPLANT FIT ANALYSIS

CROSS REFERENCE TO RELATED APPLICATION

This application is a U.S. national phase of International Patent Application No. PCT/AU2019/050664 filed on Jun. 26, 2019, which claims priority to Australian Patent Application No. 2018902290, filed in Australia on Jun. 26, 2018. The entire contents of both applications are hereby incorporated herein by this reference.

FIELD OF THE INVENTION

The present invention relates to systems and methods for surgical biological implantation, and in particular to orthopaedic hardware systems during a surgical procedure, for example a total knee replacement, total hip replacement, or hip resurfacing surgery.

The invention has been developed primarily for use in methods and systems for quality analysis of the implantation process and the predicted longevity of the orthopaedic implant within an intraoperative environment and will be described hereinafter with reference to this application. However, it will be appreciated that the invention is not limited to this particular field of use.

BACKGROUND OF THE INVENTION

Any discussion of the background art throughout the specification should in no way be considered as an admission that such background art is prior art, nor that such background art is widely known or forms part of the common general knowledge in the field in Australia or worldwide.

All references, including any patents or patent applications, cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents forms part of the common general knowledge in the art, in Australia or in any other country.

Understanding the quality and specifics of an implantation allows various changes and precautions to be taken during surgery. This can result in a multitude of patient benefits including extending the lifetime or longevity of the implantation and increasing their rate of success and recovery.

This is especially apparent in surgeries which involve the musculoskeletal system where implants are generally exposed to significant levels of stress, for example, knee or hip joints. Any medical errors committed during the implantation process can exacerbate this stress or negatively react to it which can lead to physical implications on body movement, likely accompanied by a degree of pain for the patient. Articular tissue such as cartilage, muscle and bone comprise the joints within this system that allow it to function, with the joint's performance naturally degrading as they do. By replacing some amount of this degraded tissue with a prosthetic implant, it is possible to recover some degree of lost performance.

Total knee arthroplasty is a prominent form of orthopaedic surgery where a predefined amount of hard tissue must be removed from bones participating in the knee joint using an osteotomy. Prosthetic implants are then fixed to the remaining bone to replace that which was removed. This surgery is typically required when joint tissues, such as the cartilage surrounding the femur, tibia and patella bones, starts to wear. This causes the patient's bones of the affected joint to grind against each other during normal movement and withstand increased levels of stress that would normally have been absorbed by the cartilage. By inserting a prosthetic implant onto these bones, which is designed to absorb stress in place of the original bones of the patient, the painful effects of deteriorated joint tissues can be significantly reduced.

According to the national centre for health statistics, in the US alone, over 700,000 total knee arthroplasty operations are performed annually which is expected to rise to 3.48 million by the year 2030. The vast majority of these operations are initially successful, with patients, whose mean age is 66.2 years old, reporting significantly less pain and increased mobility. However, after a duration has passed postoperatively, it is possible that issues may arise which require total knee revision surgery. This revision surgery is currently required for around 8% of all knee replacement procedures, with the total annual revisions set to increase in line with the number of yearly procedures by 2030.

Total knee revision surgery involves the removal of a pre-existing implant from the joint in question and its subsequent replacement with a new implant. This type or procedure is generally deemed to be significantly more complex in comparison to the initial joint (e.g. knee or hip) arthroplasty operation. This is partly because the implant may be well fixed, and bone loss can occur with implant removal.

A prosthetic implant can be fixed to articular hard tissue using one of two different methods. The first is by attaching it directly to the hard tissue ("press-fit") and relying on osseointegration, which refers to hard tissue naturally growing into/onto the prosthetic implant and stabilising it. The second is through a fixative such as bone cement that forms a strong bond between the prosthetic implant and hard tissue. When the implant needs to be removed, the natural bone growth or inserted fixative and any other articular tissue inhibiting removal must be destroyed.

The remaining tissue, including hard tissue such as bone, can then be sculpted using multiple osteotomies to result in dimensions that match the new prosthetic implant. However, for subsequent joint arthroplasty surgeries, depending on the amount of hard tissue that was lost during the process of removing the previous implant, the amount of remaining hard tissue may be insufficient for further tissue sculpting processes. A bone graft may be required in this scenario which is hard tissue extracted from a different area of the patient and transplanted to the implantation area. This requires preoperative planning, specialised equipment and increased surgical skill. The longevity and overall satisfaction of revision surgeries is inferior to that of the initial replacement surgeries, typically with significantly increased risk of complications and detrimental issues arising.

With respect to total knee arthroplasty surgeries, the need for total knee revision surgery is a result of one or more multiple different causes. These include aseptic loosening, infection, polyethylene wear, instability, pain, osteolysis and malposition which are responsible for 23.1%, 18.4%, 18.1%, 17.7%, 9.3%, 4.5% and 2.9% of all revision surgeries respectively. These causes are interdependent, with the appearance of one potentially being triggered or influenced by the beginnings of another.

Aseptic loosening is the largest cause of revision surgery and refers to the fixation failure at the implant and articular tissue interface, leading to increasing levels of pain and joint instability for the patient. The aetiology of aseptic loosening comprises of four main causes. Once such cause is a biological response to wear particles released from the prosthetic implant during use. Provided that enough stress is applied, it is possible that small particles within the critical range of 0.3 to 10 micrometres may detach from the implant. Depending on the health of the articular tissue and the genetics of the patient, this may then cause a macrophage-based inflammatory response, leading to osteolysis.

A different cause of aseptic loosening may be the build-up of intra-articular fluid pressure. This is a result of the overproduction of synovial fluid due to exposed hard tissue or wear particles surrounding the joint. This excess of synovial fluid creates additional pressure which may result in abnormal bone perfusion or ischemia, leading to necrosis and osteolysis.

Another cause of aseptic loosening may be the physical design of the implant wherein the pattern and profile of the surface influences the rate and potential of osseointegration. If this influence is negative, then the amount of ingrowth may not be enough to stabilise and fixate the prosthetic.

A further cause of aseptic loosening could also be the individual biological make-up of the patient which includes characteristics specific to them such as their age and habits, any pre-existing infections or diseases that may affect the joint, and their genetics. If the patient partakes in routine physical exercise, such as running, or has naturally weak joints, then their risk will increase.

Once aseptic loosening has begun to occur, attributed by any one or more of the above causes, issues such as infection and malposition will be exacerbated, along with the continued loosening of the joint prosthetic, progressing the patient further towards revision surgery.

These causes can be attributed to the prosthetic compatibility, which is defined as the correlation between the states and morphology of the implant and the underlying articular tissue.

The state determines how well the implant and articular tissue can co-exist with each other, indicating the potential for issues which may occur immediately or postoperatively. The material of the implant and the health of the tissue generally determines proper fixation.

The morphology determines how well the implant will physically attach to and impact the tissue and its form. If the implant or tissue has differing connective surfaces or forms, then the distribution of contact between them may be irregular or minimal, leading to potential issues postoperatively. This can also be the result if the connective shapes of either the implant itself or the implant receiving site are altered due to the stress caused by insertion of the implant, making once compatible morphology no longer so.

The importance of this compatibility and the risk of revision is further increased by the physiological state of the patient. If they are relatively young or maintain an active lifestyle where the implant is under constant stress, then potential new issues may be created while existing ones will be exacerbated.

This means that the quality and longevity of the implantation procedure is at least partially determined by the state and morphology of the connective components as at the time of the implant surgery and how well these attributes allow them to physically fit together. If these attributes are poor, then the risk of revision due to the prior mentioned issues is relatively high, whilst this is typically not the case or is significantly less probable if they are not. The skill and precision required by this procedure is likely the biggest reason for the difference in quality, typically being dependent on the experience and competence of the acting surgeon.

Common approaches to measuring the quality of an implantation procedure generally involve either reliance on existing instrumentation or manual observation. Existing instrumentation typically defines the desired hard tissue morphology and the different osteotomies from a fixed set of possible options required to achieve it. They work under the assumption that after the osteotomies have been executed, the remaining hard tissue will be a perfect fit for the implant.

The majority of measures used in defining these osteotomies are calculated based on inherent properties that may exist for a particular group of hard tissue, such as the mechanical axis for knee joints. This means that they are dependent on the accuracy of these inherent properties and the assumption that the structure of all related hard tissue will be the same or highly comparable. However, considering the variation between the hard tissue of different patients, such a dependency may not necessarily lead to accurate results.

The instrumentation measurements are also typically performed independent to the actual procedure. It may provide quantification of measurable attributes, but cannot, in and of themselves, ensure that the procedure has been completed successfully. This means that inconsistencies, such as how straight a particular cut is or how well aligned and positioned the instrumentation may be, can have a further effect on their accuracy. Accordingly, it is not uncommon for the finalised hard tissue morphology to have various imperfections.

The surgeon, or other operating personnel, generally use manual observation techniques to judge whether an implant fit is appropriate, or if additional alterations are needed. This judgement is built up over time based on experience with intraoperative stimuli and feedback. This may include the resistance felt upon implant insertion, visible areas that do not make contact with the inserted implant and the range and freedom of movement that the implant provides when manipulated. As most of these observations are subjective, cannot be verified, and are largely dependent on the personnel involved, their overall contribution to the implantation procedure is difficult to discern and may not be positive.

The invention herein disclosed provides a method of performing implant fit analysis and longevity prediction.

SUMMARY OF THE INVENTION

It is an object of the present invention to overcome or ameliorate at least one or more of the disadvantages of the prior art, or to provide a useful alternative.

One embodiment provides a computer program product for performing a method as described herein.

One embodiment provides a non-transitive carrier medium for carrying computer executable code that, when executed on a processor, causes the processor to perform a method as described herein.

One embodiment provides a system configured for performing a method as described herein.

The invention provides systems and methods for implant fit analysis and longevity prediction. In particular, the invention provides methods for the collection of data from different sensors, the processing and subsequent interpretation of that data, and the generation of compatibility information based on these results.

In one aspect, the invention provides systems for gathering data of differing types that may describe various attributes related to the compatibility and immediate fit quality existing between an implant and specific hard tissue based on the method of data generation. A preferred system comprises multiple different sensors and possible capture tools within a typical surgical environment where the sensors operate collectively in an automated fashion to assist the surgeon.

The selection of sensors comprises at least one sensor which may exist independently, or as part of a sensor system or set of sensors. Individual sensors may be operable to monitor, sense, and collect data on various attributes, characteristics, occurrences, or measurements, from different angles, positions, vicinities, placements, or arrangements that exist with, within or are directed at their subject which may be articular tissue, the implant, the interface between the tissue and implant, the surrounding environment, the result of an action or interaction, individual or collections of systems or devices and any other advantageous source or series of sources therewith. The sensors may be completely self-contained or may require additional devices, services, platforms, or conditions to interface with, configure, or operate appropriately. For example, devices capable of creating controlled lighting conditions such as LED lights may be necessary for some sensors. Similarly, motion platforms or otherwise manoeuvrable attachments capable of moving or repositioning a sensor could also be required.

Selected sensors may include those based on Raman spectroscopy, spectral imaging, hyperspectral imaging, optical imaging, thermal imaging, fluorescence spectroscopy, microscopy, acoustics, 3D metrology, optical coherence tomography, position, movement, balance, laser power and any other singular, combination, or sequence of sensing forms.

Sensed attributes comprise the state or morphology of the tissue or implant. State attributes may include composition, hydration, density, necrosis, colouration, reflectance, heat consistency, deterioration, particle dissolution, and any other singular, combination, or sequences of state descriptors. Morphology attributes may include shape, flatness, parallelism, roughness, waviness, peak distribution, porosity, rigidity and any other singular, combination, or sequence of morphology descriptors.

In one embodiment, the sensing may occur during the surgery. This sensing process may pause, omit, or otherwise disregard sensed data in the scenario that any obstructions occur that result in changes to viable sensing conditions which may include personnel obscuring the sensors, an overabundance of light or noise, unfavourable movement of the subject, or any other singular, combination, or sequence of adverse sensing conditions.

In another embodiment, sensing may interrupt the natural progression of a surgery for a predetermined or intraoperatively determined duration to provide an environment that is beneficial to the sensing procedure. This interruption may comprise of changes to the surgical environment that may include the temporary removal of personnel, lighting modifications or dimming, atmospheric alterations, subject repositioning or any other singular, combination, or sequence of environmental changes.

In one embodiment, sensed data may be interpreted based on the individual sensor that provided it, irrespective of other sensors which may surround or operate in relation to it.

In another embodiment, sensed data may be interpreted based on a system, set of, or multiple sets of sensors where inclusion may be coincidental or defined by attributes, similarities, conditions, states, or any other singular, combination, or sequence of grouping factors.

In another embodiment, sensed data interpreted based on collections of sensors may be summarised to provide increasingly accurate information, be used as a fault tolerance measure to determine working efficiency, or in any other singular, combination, or sequence of ways in which the unison of the involved sensors may be beneficial.

In a further embodiment, the interpretation of sensed data originating from a single, system, set of, or multiple sets of sensors may occur irrespective of, or with respect to, environmental or internal conditions, and physical sensor arrangement which may include temperature, humidity, pressure, varying amounts of lighting and their directions, different positions, angles, vicinities, or placements, or any other singular, combination, or sequence of influential factors.

In another aspect, the invention provides methods for processing sensed data into at least one different, sequential form that may increase its usability or evaluability. Preferred methods comprise cleaning the data to remove noise or redundancy, changing the format or arrangement of the data, sampling the data to segregate portions or areas which may be deemed beneficial, normalising the data to restrict it with a comparable range, decomposing the data to define its constituent elements, or aggregating them into an entity of prominent utility.

Sensed data provided by any specific selection of sensors will be dependent on those sensors, and may include particular wavelengths, signals, arbitrary numbers, equations, coordinates, models, or any other singular, combination, or sequence of directly or indirectly interpretable data forms.

The processing of sensed data may involve various different, similar, or identical methods in the same or alternating orders to produce single or multiple subsequent forms leading up to a finalised form. Some algorithms or methods may not be available for all forms of data or sensor types, although this may change provided the appropriate modifications. Each individual form may beneficially contribute to a subsequent form without necessarily being included in the final form.

Constituent elements represent independent or summarised components that exist within the original data. The number and type of constituent elements produced is dependent on the data form, any previously executed processing methods, the situation, or environment in which the sensing occurred, or any other singular, combination, or sequence of conditions which may result in multiple components existing within the data. Constituent elements of articular tissue typically comprise of cancellous bone, cortical bone, cartilage, fat, ligament, muscle, capsule, or meniscus. Additional constituent elements may exist as specialisations of these which may include composition, hydration, density, necrosis, reflectance, temperature, or any other singular, combination, or sequence of elements that could possibly describe the state of articular tissue.

In one embodiment, large sections or collections of data whose additional value may not have a significant impact on conclusions derived from the remaining data or which are incorrect or erroneous may be removed. This may include data in which the event of interest or aspects that may support it does not occur, that consists of erratic values, or any other singular, combination, or sequence of states in which the extraction of utility is impractical or negligible.

In another embodiment, sets or series of data corresponding to the same, similar, or different events which bear structural similarities may be averaged or otherwise combined to outline portions or areas where variations including noise or erroneous data may exist, which can then be removed from the either singular or combined sets or series of data.

In another embodiment, similar data that has little value individually may be summarised or combined into single or multiple representative sets of data to decrease the sheer amount of data without significantly impacting any derived conclusions.

In one embodiment, the format, form, or structure of the data may be rearranged, altered, or changed to produce additional or alternate utility through methods which may include flattening the data or changing the positions or relationships between specific or ordered values.

In one embodiment, the data may be sampled to extract areas or portions deemed more advantageous or to create a series or set of data samples that can be processed or manipulated separately for purposes such as cross validation or testing.

In one embodiment, the data may be normalised through algorithms and methods such as constant shifts, smoothing, scaling, standard normal variate, baseline correction, continuum removal, or any other singular, combination, or sequence of algorithms and methods capable of improving data consistency.

In one embodiment, the data may be decomposed or deconvoluted into its constituent elements or features which may be achieved through algorithms and methods including the automatic target generation process, pixel purity index, N-FINDR, independent component analysis, non-linear least squares, fuzzy k-means, or any other singular, combination, or sequence of algorithms and methods capable of decomposition. Some of these algorithms and methods may not be possible without potential modification depending on the form of the supplied data and its purpose.

In another embodiment, constituent elements may be identified prior to beginning their extraction to determine those that exist within the data and any directives that may assist in their extraction.

In another embodiment, a series or set of constituent elements may be averaged or combined in a beneficial manner provided they share or do not share any similar patterns or other elements which can be used as a means of grouping. This may occur when the number of constituent elements is greater than the expected number.

In a further embodiment, decomposition may comprise the removal of data dimensions to reduce complexity or computational load. This may be performed through algorithms and methods including decision trees, random forests, high correlation filters, backward feature elimination, factor analysis, principal component analysis, linear discriminant analysis, generalised discriminant analysis, or any other singular, combination, or sequence of algorithms and methods capable of removing dimensions.

In one embodiment, the representative, constituent, or otherwise singular sets of data, elements, or features may be aggregated together into a single entity or into fewer entities that can be processed more easily whilst maintaining similar or increased utility.

In another aspect, the invention provides methods of interpreting processed data into at least one different subsequent form that may increase its utility. A preferred method comprises calculating custom or standardised mathematical or statistical measures, provisioning by external parties or internal controllers, and the training and execution of machine learning, data science and mathematical algorithms and methods.

The interpretation of processed data may involve various different, similar or identical methods in the same or alternating orders to produce single or multiple subsequent forms leading up to a finalised form. Some algorithms and methods may not be available for all forms of data or sensor types, although this may change provided the appropriate modifications. Each individual form may beneficially contribute to a subsequent transformation without necessarily being included in the final form.

In one embodiment, measurements defined by mathematical or statistical equations, theories, or concepts such as the mean, standard deviation, and variance may be calculated to gain insight into summarised information based on the processed data.

In another embodiment, measurements defined by standards authorities such as the international standards organisation (ISO) or those that are custom to a specific subject or environment relating to the processed data may be calculated to gain insight into specific attributes or characteristics such as surface flatness and roughness.

In one embodiment, previous medical records or history relating directly or indirectly to the specific patient may be provided.

In another embodiment, explicit information relating to an implant or other fixed or manufactured entity may be provided directly by the company responsible for their production or manufacturing.

In another embodiment, preoperative scans, investigations, or precursor operations with the intent of developing further information relating to a specific issue or problem may be provided.

In a further embodiment, trained medical staff or otherwise personnel with verifiable ability can provide observations or tacit conclusions surrounding or relating to the subject either directly or indirectly based on the currently accessible and prior knowledge.

In one embodiment, control units responsible for managing a specific sensor or collection of sensors may provide analysis results from internally collected and processed data.

In one embodiment, processed data may require additional processing or manipulation prior to being provided to a single or multiple machine learning, data science, or mathematical algorithms and methods.

In another embodiment, a single or set of processed data may be used to train a single or multiple machine learning, data science, or mathematical algorithms and methods.

In a further embodiment, processed data may be provided to a single or set of trained machine learning, data science, or mathematical algorithms and methods to produce corresponding output.

In another aspect, the invention provides methods of generating compatibility information based on the interpreted data of a tissue, an associated prosthetic implant, and the interface between them. A preferred method comprises generating the degree of compatibility, analysing the impact from implant insertion or fixation, evaluating the implant fit, and predicting the longevity and performance of the implant.

The generation of compatibility information may involve various different, similar, or identical methods in the same or alternating orders to produce single or multiple subsequent forms leading up to a finalised form. Some algorithms or methods may not be available for all forms of data or sensor types, although this may change provided the appropriate modifications. Each individual form may beneficially contribute to a subsequent transformation without necessarily being included in the final form.

Compatibility information comprises any analysis or conclusions which may describe the quality of the interface between a specific tissue and an associated implant before, immediately after, and some duration after implantation. This includes how the state or biology of the tissue and implant may interact with each other, the physical connectivity of the two in terms of their morphology, the accuracy of the insertion, and the longevity of the interface when these factors and the nature of the individual being operated on is taken into account.

The interface between a prosthetic implant and tissue can either rely on bone ingrowth through a process known as osseointegration or can be artificially created through a fixative such as bone cement.

In one embodiment, the health of the tissue and patient may be considered to determine the fixation potential and subsequent survivability of the connective interface.

In one embodiment, the material comprising the prosthetic implant may be compared against the tissue state and any required fixative to determine if any adverse reactions may occur both intraoperatively and postoperatively.

In another embodiment, the lifestyle of the patient including their level of activity and daily routines may be considered to determine the stress that the prosthetic implant and connective interface may endure.

In one embodiment, the shape and form of the implant may be compared to that of the tissue to determine the possibility and difficulty of insertion.

In another embodiment, the degree and distribution of contact that the implant will make against the tissue upon insertion may be determined to gauge fixation potential and the longevity of the connective interface.

In one embodiment, any surface breakage, density reduction, or other effects to the tissue or implant upon insertion may be determined to inform other measures and comparisons so that compatibility information may be adjusted accordingly.

In another embodiment, the spreading or dislocation of any fixative applied to the implant or tissue upon insertion may be determined to ensure that a sufficient distribution remains that can achieve an appropriate fixation.

In one embodiment, the ideal fit of the implant against the tissue may be calculated and compared to its actual fit to determine the amount of deviation.

In another embodiment, changes to the position and rotation of the inserted implant may be applied to increase the quality of the implantation and result in less deviation when compared to the calculated ideal fit.

In one embodiment, generated compatibility and verified implantation longevity and performance data may be used to train machine learning, data science, or mathematical algorithms and methods.

In another embodiment, verified implantation longevity and performance data may be retrieved from previous consenting patients who have had their implant for a set duration under specific conditions.

In another embodiment, machine learning, data science, and mathematical algorithms or methods may be based around supervised approaches. These algorithms or methods may include linear and polynomial regression, logistic regression, naïve bayesian networks, bayesian networks, support vector machines, decision trees, random forests, k-nearest neighbour classifiers, neural networks, and any other singular, combination, or sequence of supervised approaches.

In one embodiment, compatibility data may need to be processed to achieve a more evaluable form using algorithms and methods which may include those stated in the second aspect of this invention.

In one embodiment, the verified data pool will be split into at least two divisions where these splits are not necessarily even or proportional.

In another embodiment, a single or set of split verified data may be provided into a single or multiple machine learning, data science, or mathematical algorithms or methods in a sequential, simultaneous, or periodic manner.

In another embodiment, a single or set of all or a portion of the remaining split verified data may be provided into previously trained single or multiple machine learning, data science, or mathematical algorithms and methods to gauge the accuracy of the corresponding output against the externally confirmed output.

In another embodiment, the accuracy of a particular trained machine learning, data science, or mathematical algorithm and method may be gauged as sufficient depending on its statistical significance which may be influenced or defined by the application of its predictions or estimations.

In a further embodiment, if the accuracy is not proven to be sufficient, then the verified data selected, its input procedure, the single or multiple machine learning, data science, or mathematical algorithms and methods, and any other singular, combination, or sequence of causation may be modified, removed, rearranged, or added to possibly result in increased accuracy.

In one embodiment, compatibility data may be provided to a single or set of trained machine learning, data science, or mathematical algorithms or methods to produce corresponding output.

In another embodiment, corresponding output from at least two machine learning, data science, or mathematical algorithms or methods may be averaged, combined, or compared to possibly reach increasingly definitive conclusions.

In one embodiment, simulations may be constructed to test the entirety of, or collections of, available data under various conditions which may provide insight into phenomena such as the impact of implant insertion and varying levels of stress applied to the connective interface.

In one embodiment, corrective information for altering the tissue morphology is generated to inform the surgeon of the set of actions desirable to improve the implantation performance and longevity.

In one embodiment, the corrective information samples different possible sets of actions against predicted postoperative implant performance.

In another embodiment, the corrective information includes a numerical quantification of the implantation performance and longevity for the currently existing and subsequently resulting tissue morphology after the proposed set of actions has been performed.

In another embodiment, the corrective information has a preconfigured threshold beyond which corrective actions may be identified as infeasible given the surgical cutting technique being applied and its inherent inaccuracies.

Accordingly, it is evident that the current methods used for measuring and ensuring implantation quality, despite being suboptimal, are still frequently used. Therefore, there is a need for improved systems and methods for measurement of critical parameters and assessment of prosthesis survivability for an orthopaedic procedure and also for systems and methods for use by the surgeon during an orthopaedic prosthesis implantation procedure to maximise prosthesis integration and survivability for the long-term benefit of the patient.

According to a first aspect of the invention, there is provided a method for intraoperative implant fit analysis and longevity prediction for a prosthetic implant to be integrated with the physiological tissue of a patient. The method may comprise the step of collecting data via a plurality of sensors situated in proximity to the tissue and implant and a plurality of data sources. The method may comprise the further step of determining tissue and implant state and morphology based on the collected data. The method may comprise the further step of generating compatibility information between the tissue and implant based on the determined tissue and implant state and morphology. The method may comprise the further step of processing compatibility information into a form adapted for evaluation against a pre-determined comparator. The method may comprise the further step of generating a means of predicting postoperative implant performance and longevity utilising the historical dataset of comparison information and postoperative results. The method may comprise the further step of generating and providing corrective information for alteration of the tissue state and morphology for improved postoperative implant performance and longevity.

According to a particular arrangement of the first aspect, there is provided a method for intraoperative implant fit analysis and longevity prediction for a prosthetic implant to be integrated with the physiological tissue of a patient, comprising the steps of: collection of data via a plurality of sensors situated in proximity to the tissue and implant and a plurality of data sources; determining tissue and implant state and morphology based on the collected data; generating compatibility information between the tissue and implant based on the determined tissue and implant state and morphology; processing compatibility information into a form adapted for evaluation against a pre-determined comparator; generating a means of predicting postoperative implant performance and longevity utilising the historical dataset of comparison information and postoperative results; and generating and providing corrective information for alteration of the tissue state and morphology for improved postoperative implant performance and longevity.

The tissue may comprise biological tissue including bone. The prosthetic implant may comprise a knee prosthetic, or a hip prosthetic. The prosthetic implant may comprise one or more features comprising threading or patterns on one or more surfaces to encourage osseointegration and/or increase the rigidity of the fixation to the tissue.

The sensors may comprise at least one sensor that exists independently or as part of a sensor system or set of sensors. The sensors may comprise at least one sensor that is completely self-contained.

The sensors may comprise at least one sensor that requires additional devices, services, conditions, platforms or any other single, combination or sequence of requirements to be interfaced with, configured or operated appropriately.

The sensors may comprise at least one sensor that is individually configured to monitor, sense, collect, and provide data based on various properties, characteristics, occurrences or measures from different angles, positions, proximities, vicinities, movements, speeds, placements or arrangements that exist with, within or are directed by their subject.

The subject may comprise one or more of the tissue, the implant, the connective interface, the surrounding environment, the result of an action or interaction, individual or collections of systems or devices and any other source or series of sources therewith.

The subject may be treated, altered, or conditioned in order to affect its original, initial or current state for the purpose of preservation, identification, unification, fixation or any other single, combination or sequence of objectives.

The subject may be modified structurally, chemically or through any other single, combination or sequence of approaches which may change its form as part of or independent to any intraoperative procedures, surgeries or any other single, combination or sequence of medical operations.

The sensors may be configured to work in an automated fashion, through manual triggering or through any combination or sequence of manual and automatic triggering.

Manual triggering may comprise a manual trigger including buttons, voice commands, gesture controls, or alternate physical actuation.

The sensors may be configured to engage in sensing indefinitely, periodically, singularly or in any other single, combination or sequence of sensing approaches as influenced by the situation, environment, user control, sensor configuration and any other single, combination or sequence of variables capable of having a direct or indirect effect.

The sensing may be configured to work in real-time, near real-time, through some form of delayed processing or in any other single, combination or sequence of processing approaches which may be influenced by the situation, environment, user control, sensor configuration and any other single, combination or sequence of variables capable of having a direct or indirect effect.

The sensors may require external involvement to operate correctly including changes to its position, angle, vicinity, proximity, configuration, lighting, timing or any other single, combination or sequence of sensor, situational or environment changes.

Data sources may comprise records, files, databases, systems, or any other single, combination, or sequence of internal or external data sources which may have been verified or validated.

Tissue state may comprise one or more of composition, hydration, density, necrosis, colouration, reflectance, and temperature. Implant state may comprise one or more of composition, deterioration, density, and particle dissolution. Tissue and implant morphology may comprise one or more of shape, flatness, parallelism, roughness, waviness, peak distribution, porosity, rigidity. Determination of tissue and implant state and morphology may comprise at least one action of work relating to the processing of sensed data.

The processing of sensed data may comprise cleaning the data including the removal or fixing of any noise, erroneous or redundant data and any other single, combination or sequence of processes adapted to remove negligent data or increase the overall utility of the remaining data.

The processing of sensed data may comprise formatting the data including the rearrangement of data into a more appropriate structure or form, the flattening of data or extraction from its current storage.

The processing of sensed data may comprise sampling the data including the selection or division of portions of said data.

The processing of sensed data may comprise the scaling or alignment of data so that its values are within a comparable range or achieve some additional level of comparability.

The processing of sensed data may comprise the decomposition or deconvolution of said data so that representative or otherwise specific features or portions of data can be split into constituent elements or elements which provide more utility individually.

The processing of sensed data may comprise the aggregation of said data so that individual features, constituent elements, sections or portions of data may be combined into a single entity.

The processing of sensed data may comprise at least one action of work relating to any other single, combination or sequence of processes, manipulations, generations, alterations or any other functions that may better prepare said data for usage.

The processing of sensed data may be either not performed or partially performed if an additional entity such as a sensor controller or bridging device has performed this processing individually or independently.

The determination of tissue and implant state and morphology may comprise at least one action of work relating to the interpretation of the processed data.

The interpretation of processed data may comprise at least one action of work relating to any general or specific mathematical equations, theories, calculations, concepts or any other single, combination or sequence of mathematical functions.

The interpretation of processed data may comprise at least one action of work relating to the execution of processes or functions which calculate custom or standardised geometrical, morphological, structural or any other single, combination or sequence of related measures.

The interpretation of processed data may comprise at least one action of work relating to the execution of machine learning, data science or mathematical algorithms or methods.

The interpretation of processed data may be either not performed or may be partially performed if an additional entity such as a sensor controller or bridging device has performed this interpretation individually or independently.

The interpretation of processed data may comprise at least one action of work relating to any observations or tacit conclusions provided by verified personnel. The interpretation may be explicitly provided through medical records or history, preoperative procedures or any other single, combination or sequence of forms which may be independent to any generated or processed data. The interpretation of processed data may comprise at least one action of work relating to any other single, combination or sequence of processes, equations, generations, alterations, or any other forms of interpretation.

According to particular aspects and embodiments as disclosed here, generating compatibility information may be based on interpreted data from the tissue comprising a receiving surface, an associated implant comprising an engaging surface and the interface between them, the interface comprising the contact between the receiving surface and the engaging surface, according to any one of the preceding claims. Generating compatibility information may comprise the steps of: generating the degree of compatibility of the interface with either or both the receiving surface and the engaging surface; analysing the impact of implant insertion or fixation; evaluating the implant fit; and predicting the longevity and performance of the implant.

Generating the degree of compatibility may comprise at least one action of work related to the comparison of the determined tissue and implant state and morphology.

The comparison of the determined tissue and implant state and morphology may comprise at least one action of work related to gauging the compatibility of the tissue and implant state.

Gauging the compatibility of the tissue and implant state may comprise determining if the implant material is appropriate for the tissue.

Implant material appropriateness may comprise the potential for adverse reactions occurring at any time and duration including intraoperatively or postoperatively.

Implant material appropriateness may comprise the intended or possible fixation material, substance, process or any other single, combination or sequence of fixatives or fixation approaches.

Implant material appropriateness may comprise the possible stress, pressure, intended usage scenarios and any other single, combination or sequence of occurrences or situations that the implant may endure postoperatively.

Gauging the compatibility of the tissue and implant state may comprise checking the health of the tissue to measure fixation potential and survivability.

The comparison of the determined tissue and implant state and morphology may comprise at least one action of work related to gauging the compatibility of the tissue and implant morphology.

Gauging the compatibility of the tissue and implant morphology may comprise determining if the shape and form of the tissue will enable the implant to be inserted and the difficulty therewith.

Gauging the compatibility of the tissue and implant morphology may comprise determining the degree of contact that the implant will make against the tissue when inserted and the distribution that this will have.

Gauging the compatibility of the tissue and implant morphology may comprise determining the degree in which the surface of the tissue populates the threading of the implant and how comparable the distribution pattern of the tissue within this threading is in comparison.

Analysing the impact of implant insertion or fixation may comprise determining the likely effect that inserting the implant will have on the tissue or implant.

The effect of inserting the implant on the tissue may comprise surface breakage, density reduction or any other single, combination or sequence of surface or state alterations.

Any surface alterations may influence the process or results of at least one other single, combination or sequence of methods or techniques of gauging the compatibility degree not limited to those explicitly stated.

The effect of inserting the implant onto tissue may comprise spreading, distributing or affecting any single or combination of applied fixatives that may be directly or indirectly present.

Evaluating the implant fit may comprise comparing its current placement against a calculated ideal placement. Placement may be defined by the degree of contact between the tissue and implant, the population and pattern of tissue within the implant threading, the stress distribution on the implant and any other single, combination or sequence of qualitative or quantitative measures, properties or characteristics of surface contact. The ideal placement may be defined by beneficial or advantageous values of properties or characteristics used to describe implant placement.

The quality of implant fit may be influenced by the implant and tissue state and morphology, the situation and environment, the intended usage scenarios and stress that the implant will endure, and any other single, combination or sequence of qualitative or quantitative measures, properties or characteristics of mechanical or structural force.

The results of the evaluation may not be explicit and may provide quantitative or qualitative measures based on all available information adapted to allow for informed judgement.

Various recommendations, critiques, indicators, prompts or any other single, combination or sequence of approaches may be used to inform an entity about the necessary changes required to make the current position closer to the calculated ideal position.

Performing additional analysis in the event of repositioning, movement, rotation, or any other single, combination or sequence of changes to the current position of the implant resulting in changes to the degree of compatibility.

Predicting the longevity and performance of the implant may comprise at least one action of work related to the consideration of generated compatibility information, tissue and implant state and morphology, fixation approaches, previous medical history or records, intended usage, implant stress levels, and any other single, combination or sequence of information adapted to assist in or support the prediction.

Implant longevity and performance may comprise quantitative measures of time and qualitative measures relating to the ease of performing certain tasks and any other single, combination or sequence of measures adapted to provide additional insight.

Generated implant longevity and performance information may be used directly or may be interpreted so as to produce recommendations based on the usage or the current lifestyle of the patient.

Predicting the longevity and performance of an implant may comprise at least one action of work related to the execution of a machine learning, data science or mathematical entity, concept, model, equation or any other single, combination or sequence of embodiments.

At least one simulation or any other computational method or entity may be used to predict, generate, calculate, verify, validate or any other single, combination or sequence of usages adapted to result in information or utility.

The processing of compatibility information or data may comprise at least one action of work relating to the transformation of said compatibility information or data into an evaluable form.

The transformation of data may comprise at least one action of work involving a single, multiple, combination or sequence of pre-processing steps.

A pre-processing step may comprise cleaning the data including the removal or fixing of any noise, erroneous or redundant data and any other single, combination or sequence of processes which adapted to increase the utility of the remaining data. The pre-processing step may comprise formatting the data including the rearrangement of data into a more appropriate structure or form, the flattening of data or extraction from its current storage, and any other single, combination or sequence of formatting adapted to increase the usability of the data.

The pre-processing step may comprise sampling the data including the selection or division of portions of data and any other single, combination or sequence of processes adapted to result in more representative or advantageous data.

The transformation of data may comprise at least one action of work involving a single, multiple, combination or sequence of raw or pre-processed data manipulations.

The manipulation of raw or pre-processed data may comprise scaling or alignment of said data so that their values are either within a comparable range or achieve some additional level of comparability.

The manipulation of raw or pre-processed data may comprise decomposition of said data in order to split representative or otherwise specific features or portions of data into constituent elements or elements providing improved more utility than individually.

The manipulation of raw or pre-processed data may comprise aggregation of said data in order to combine individual features, constituent elements, sections or portions of data into a single entity.

The transformation of data may comprise at least one action of work relating to any other single, combination or sequence of processes, manipulations, generations, alterations or any other functions adapted to prepare said data for usage or evaluation.

The comparator may comprise a set of data in a similar or otherwise comparable form belonging to a single, combination or sequence of comparison information.

Postoperative results may be received from a patient after a duration of time has occurred. The received postoperative results may undergo at least one action of work as described above.

Generating a means of predicting postoperative implant performance may comprise training a machine learning, data science or mathematical entity, concept, model, equation or any other single, combination or sequence of embodiments configured to provide performance predictions.

Any machine learning, data science or mathematical entity, concept, model, equation or any other single, combination or sequence of embodiments may be augmented with the inclusion of new data.

Generating corrective information for altering the tissue morphology and providing the generated corrective information comprising a set of actions may be adapted to improve the implantation performance and longevity to the surgeon.

The corrective information may comprise a sample of different possible sets of actions against predicted postoperative implant performance.

The corrective information may comprise a numerical quantification of the implantation performance and longevity for the currently existing and subsequently resulting tissue morphology after the proposed set of actions has been performed.

The corrective information may comprise a preconfigured threshold beyond which corrective actions may be identified as infeasible given the surgical cutting technique being applied and its inherent inaccuracies.

The method of any one of the preceding claims, wherein the sensed, raw, pre-processed, manipulated, processed, interpreted, usable, evaluable or any other single, combination or sequence of generated, derived or received data is stored electronically including either offline, online or through a combination of the two for later retrieval, processing, or any other single, combination or sequence of forms of usage.

Any at least one action of work may be influenced, effected, adjusted or directed by patient specific deformations or issues which comprising one or more of vargus or varus errors, mechanical alignment errors, or any other errors adapted to cause the physiological structure of a patient to differ to that which is considered normal or ideal.

At least one action of work may occur within an intra-operative environment. At least one action of work may occur in the same, different or alternating order and adapted to produce the same, similar, or different finalised result. At least one action of work may occur in real-time, near real-time, through a delayed processing procedure or in any other single, combination or sequence of processing approaches.

Data processing or data storage required may occur either internally, externally on a centralised, decentralised or otherwise online entity or any other single, combination or sequence of computational approaches.

According to a second aspect of the invention, there is provided a system for supporting a surgical biological implantation procedure for integration of a prosthetic device with a patient's tissue. The system may comprise one or more sensors for sensing characteristics of the patient's tissue morphology to collect at least state and morphology data generate collected data comprising. The system may further comprise one or more processors. The one or more processors may be adapted for pre-processing and manipulation of the collected data to generate processed data, said processed data having a form suitable for interpretation. The one or more processors may be further adapted for interpreting the processed data for extraction of a data representation of structure of the patient tissue and the prosthetic device. The one or more processors may be further adapted for determining compatibility data between the data representation of the patient tissue and the data representation of the prosthetic device to determine the compatibility of a connective surface of the implant with the state of a receiving surface of the patient's tissue. The one or more processors may be further adapted for predicting the longevity and performance of the prosthetic device using the compatibility data. The one or more processors may be further adapted for generating corrective data for modification of the receiving surface of the patient's tissue for improved prediction of the longevity and performance of the prosthetic device.

According to a particular arrangement of the second aspect, there is provided a system for supporting a surgical biological implantation procedure for integration of a prosthetic device with a patient's tissue comprising: one or more sensors for sensing characteristics of the patient's tissue morphology to collect at least state and morphology data generate collected data comprising; one or more processors adapted for: pre-processing and manipulation of the collected data to generate processed data, said processed data having a form suitable for interpretation; interpreting the processed data for extraction of a data representation of structure of the patient tissue and the prosthetic device; determining compatibility data between the data representation of the patient tissue and the data representation of the prosthetic device to determine the compatibility of a connective surface of the implant with the state of a receiving surface of the patient's tissue; predicting the longevity and performance of the prosthetic device using the compatibility data; and generating corrective data for modification of the receiving surface of the patient's tissue for improved prediction of the longevity and performance of the prosthetic device.

The one or more sensors may be selected from the group comprising Raman spectroscopy, spectral imaging, hyperspectral imaging, optical imaging, thermal imaging, fluorescence spectroscopy, microscopy, acoustics, 3D metrology, optical coherence tomography, position, movement, or balance sensors.

The one or more sensors may be adapted to sense attributes of the state and/or morphology of the patient's tissue and/or the prosthetic implant.

The sensed state attributes of the patient's tissue and/or the prosthetic implant may be selected from one or more of the group of composition, hydration, density, necrosis, colouration, reflectance, heat consistency, deterioration, particle dissolution, and any other singular, combination, or sequences of state descriptors.

The sensed morphology attributes of the patient's tissue and/or the prosthetic implant may be selected from one or more of the group of shape, flatness, parallelism, roughness, waviness, peak distribution, porosity, rigidity and any other singular, combination, or sequence of morphology descriptors.

The system may further comprise means for outputting the prediction of the longevity and performance of the prosthetic device.

The system may further comprise means for outputting the generated corrective data for modification of the receiving surface of the patient's tissue for improved prediction of the longevity and performance of the prosthetic device.

The collected data may further comprise historical data including historical surgical procedure record data and/or historical patient data.

The pre-processing and manipulation of the collected data may comprise one or more of; means for removing noisy, erroneous or redundant data; means for formatting the data to an appropriate data format; means for sampling the collected data into one or more representative segments; means for scaling or aligning the data; decompose the data into constituent elements; means for aggregate the data to create a statistically significant data structure.

According to a third aspect of the invention, there is provided a system for intraoperative implant fit analysis and longevity prediction for a prosthetic implant to be integrated with the physiological tissue of a patient, comprising:
  one or more processors;
  memory coupled to the one or more processors and configured to store instructions, which, when executed by the one or more processors, causes the processors to perform operations comprising:
    collection of data via a plurality of sensors situated in proximity to the tissue and implant and a plurality of data sources;
    determining tissue and implant state and morphology based on the collected data;
    generating compatibility information between the tissue and implant based on the determined tissue and implant state and morphology;
    processing compatibility information into a form adapted for evaluation against a pre-determined comparator;
    generating a means of predicting postoperative implant performance and longevity utilising the historical dataset of comparison information and postoperative results; and
    generating and providing corrective information for alteration of the tissue state and morphology for improved postoperative implant performance and longevity.

According to a fourth aspect of the invention, there is provided a non-transitory computer-readable storage device having instructions stored thereon, which, when executed by a processor, cause the processor to perform operations for intraoperative implant fit analysis and longevity prediction for a prosthetic implant to be integrated with the physiological tissue of a patient, said operations comprising:
  collection of data via a plurality of sensors situated in proximity to the tissue and implant and a plurality of data sources;

determining tissue and implant state and morphology based on the collected data;

generating compatibility information between the tissue and implant based on the determined tissue and implant state and morphology;

processing compatibility information into a form adapted for evaluation against a pre-determined comparator;

generating a means of predicting postoperative implant performance and longevity utilising the historical dataset of comparison information and postoperative results; and generating and providing corrective information for alteration of the tissue state and morphology for improved postoperative implant performance and longevity.

According to a fifth aspect of the invention, there is provided a computer program element comprising computer program code means to make a computer execute a procedure comprising:

collection of data via a plurality of sensors situated in proximity to the tissue and implant and a plurality of data sources;

determining tissue and implant state and morphology based on the collected data;

generating compatibility information between the tissue and implant based on the determined tissue and implant state and morphology;

processing compatibility information into a form adapted for evaluation against a pre-determined comparator;

generating a means of predicting postoperative implant performance and longevity utilising the historical dataset of comparison information and postoperative results; and generating and providing corrective information for alteration of the tissue state and morphology for improved postoperative implant performance and longevity.

According to a sixth aspect of the invention, there is provided a computer readable medium, having a program recorded thereon, where the program is configured to make a computer execute a procedure comprising:

collection of data via a plurality of sensors situated in proximity to the tissue and implant and a plurality of data sources;

determining tissue and implant state and morphology based on the collected data;

generating compatibility information between the tissue and implant based on the determined tissue and implant state and morphology;

processing compatibility information into a form adapted for evaluation against a pre-determined comparator;

generating a means of predicting postoperative implant performance and longevity utilising the historical dataset of comparison information and postoperative results; and generating and providing corrective information for alteration of the tissue state and morphology for improved postoperative implant performance and longevity.

BRIEF DESCRIPTION OF THE DRAWINGS

Notwithstanding any other forms which may fall within the scope of the present invention, a preferred embodiment/preferred embodiments of the invention will now be described, by way of example only, with reference to the accompanying drawings in which:

FIG. 9, including

DEFINITIONS

Figure 1:
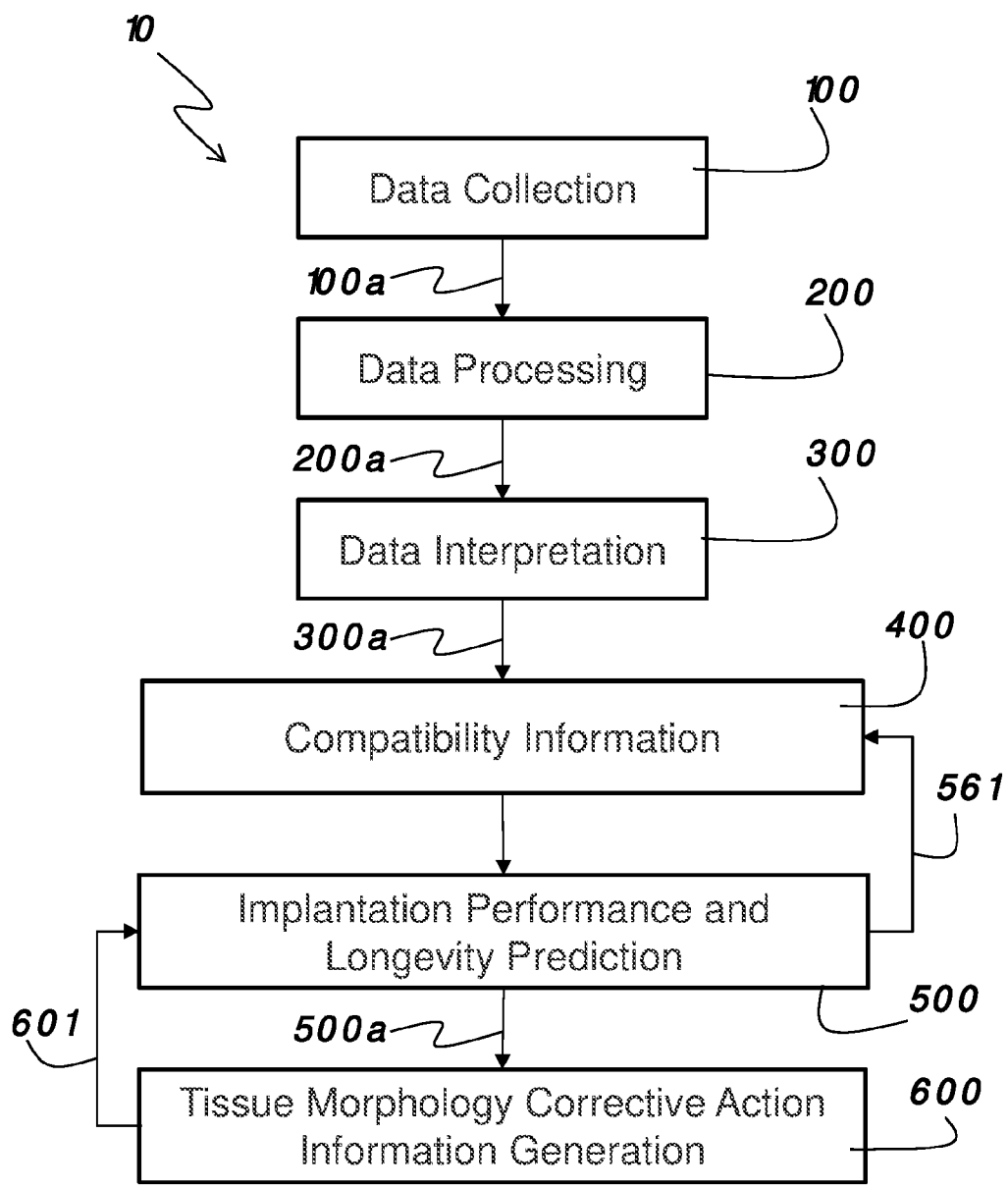
FIG. 1 is a schematic flow diagram depicting the implant fit analysis process comprising the steps required for the complete implementation of the preferred embodiment.

The following definitions are provided as general definitions and should in no way limit the scope of the present invention to those terms alone, but are put forth for a better understanding of the following description.

Unless defined otherwise, all technical and scientific terms used herein have the same meaning as commonly understood by those of ordinary skill in the art to which the invention belongs. It will be further understood that terms used herein should be interpreted as having a meaning that is consistent with their meaning in the context of this specification and the relevant art and will not be interpreted in an idealized or overly formal sense unless expressly so defined herein. For the purposes of the present invention, additional terms are defined below. Furthermore, all definitions, as defined and used herein, should be understood to control over dictionary definitions, definitions in documents incorporated by reference, and/or ordinary meanings of the defined terms unless there is doubt as to the meaning of a particular term, in which case the common dictionary definition and/or common usage of the term will prevail.

For the purposes of the present invention, the following terms are defined below.

The articles "a" and "an" are used herein to refer to one or to more than one (i.e. to at least one) of the grammatical object of the article. By way of example, "an element" refers to one element or more than one element.

The term "about" or "approximately" is used herein to refer to quantities that vary by as much as 30%, preferably by as much as 20%, and more preferably by as much as 10% to a reference quantity in the positive and negative directions of their subject unless stated or specified otherwise. The use of the terms "about" or "approximately" to qualify a number is merely an express indication that the number is not to be construed as a precise value.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Any one of the terms: "including" or "which includes" or "that includes" as used herein is also an open term that also means including at least the elements/features that follow the term, but not excluding others. Thus, "including" is synonymous with and means "comprising".

In the claims, as well as in the summary above and the description below, all transitional phrases such as "comprising," "including," "carrying," "having," "containing," "involving," "holding," "composed of," and the like are to be understood to be open-ended, i.e., to mean "including but not limited to". Only the transitional phrases "consisting of" and "consisting essentially of" alone shall be closed or semi-closed transitional phrases, respectively.

The term, "real-time", for example "displaying real-time data," refers to the display of the data without intentional delay, given the processing limitations of the system and the time required to accurately measure the data.

The term, "near-real-time", for example "obtaining real-time or near-real-time data" refers to the obtaining of data either without intentional delay ("real-time") or as close to real-time as practically possible (i.e. with a small, but minimal, amount of delay whether intentional or not within the constraints and processing limitations of the of the system for obtaining and recording or transmitting the data.

Although any methods and materials similar or equivalent to those described herein can be used in the practice or testing of the present invention, preferred methods and materials are described. It will be appreciated that the methods, apparatus and systems described herein may be implemented in a variety of ways and for a variety of purposes. The description here is by way of example only.

As used herein, the term "exemplary" is used in the sense of providing examples, as opposed to indicating quality. That is, an "exemplary embodiment" is an embodiment provided as an example, as opposed to necessarily being an embodiment of exemplary quality for example serving as a desirable model or representing the best of its kind.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or", as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one", in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

For the purpose of this specification, where method steps are described in sequence, the sequence does not necessarily mean that the steps are to be carried out in chronological order in that sequence, unless there is no other logical manner of interpreting the sequence.

In addition, where features or aspects of the invention are described in terms of Markush groups, those skilled in the art will recognise that the invention is also thereby described in terms of any individual member or subgroup of members of the Markush group.

DETAILED DESCRIPTION

It should be noted in the following description that like or the same reference numerals in different embodiments denote the same or similar features.

The following detailed description is an exemplification of the invention and should not be limited in scope by the embodiments depicted nor should it be understood in any way to be a restriction on the broad description of the invention as set out hereinbefore. These embodiments are described in sufficient detail to allow those skilled in the art to practise or exercise the invention. The precise shape, size and appearance of the components described or illustrated are not expected of nor required from the invention unless stated otherwise. It is to be understood that any utilisation, combination or structural, logical, electrical and mechanical changes, variations, augmentations or modifications to any of the mentioned or otherwise related embodiments may be made without departing from the scope of the invention. Similarly, any functionally equivalent products, compositions and methods will also remain within this scope along with all singular, combination and sequences of steps, features, structures, sequences, processes, combinations and compounds referred to or indicated within this description either singularly or collectively.

The entire disclosure of all documentation including patents, patent applications, journal articles, laboratory manuals, books, charts, repositories, and any other form of documentation or otherwise referenced resources cited herein is by no means an admission of prior art, prior or common knowledge required by those skilled in the art or any other connections or assumptions towards the invention unless mentioned otherwise.

Features presented through the drawings are referenced using the numerical ordering of the invention stage that they belong to alongside their logical ordering within the drawing itself, with the exception of the first drawing which acts as the initial overview.

The invention will be described in terms of embodiments that relate to analysing a specific portion of orthopaedic hard tissue and a corresponding prosthetic implant to determine the potential quality of their resultant connective interface, the impact caused from the connection procedure, any changes that may be required once connected and the performance and longevity of this connection based on previous operations. However, the invention has applicability more generally in the area of analysing a specific portion of tissue against an entity designed to fit or be placed in relation to it.

With advancements in sensor technology and modern processing techniques large amounts of data has become readily available and can be processed in ways that allow meaningful information to be extracted. Sensors including optical, acoustic, three-dimensional, two-dimensional, environmental, and situational sensors can be combined and configured to provide data on their respective subjects.

This data can then be processed to derive insights and conclusions that would otherwise have not been known. Numerous machine learning, data science, and mathematical algorithms and techniques exist to achieve this processing, with each being dependent on properties of the data including its amount, number of dimensions, precision, and redundancy.

Statistical analysis is one such category of these data processing techniques, which typically aims to summarise and produce measurements from sets of data or the entire data pool as a whole. These measurements generally provide insight into different characteristics of the data, such as the mean, standard deviation, variance, median, and range.

Supervised machine learning is another category of data processing techniques, which typically aims to find patterns or trends existing within specific sets of data to use as indicators to map the data to an associated value. This means that the algorithm can search new data when provided to find the same, or similar, indicators to predict the associated values. This allows it to draw meaning from data, including optical and acoustic signals, wherein statistical measures such as the mean or standard deviation would have little significance. This generally works by first training the machine learning algorithm or technique and then executing it on new data.

Training consists of processing sets of data and then using them along with their associated ground truth to build an internalised model. The training process is generally split into two different phases, the pre-processing phase and the manipulation phase. Pre-processing consists of the cleaning, rearranging, formatting and deconvolution of data to achieve a more usable form. Manipulation consists of scaling or aligning the pre-processed data, decomposing it into its constituent or representative elements and then aggregating the result if necessary. The resultant data can then be used to generate the model by finding any patterns or trends within it and creating a mapping between them and the associated ground truth of the data.

Execution consists of providing the trained algorithm with new data whose associated value is unknown. The algorithm will then process this data in a similar manner to the training phase and find any patterns or trends that exist within it that are similar to those it has already seen. It will then match the new data against an associated value based on these similar indicators.

The embodiments of the invention disclosed herein aim to improve systems and methods for use by the surgeon during an orthopaedic prosthesis implantation procedure to maximise prosthesis integration and survivability by offering alternative procedures that significantly reduces reliance on inaccurate measuring equipment; provides support to involved personnel during placement; and makes educated predictions about the potential issues and longevity of the resulting connective interface.

This is achieved by utilising an approach that revolves around using various sensors, for example, physiological and/or optical sensors, in conjunction with data retrieved and stored across numerous surgeries. The sensors of differing types produce data based on a single or combination of subjects which can be processed and interpreted to extract information that cannot be procured manually. This is supported by algorithms and methods trained from historically generated data and associated information which can predict the end result of the involved subjects when given the same input in relation to them.

It should be appreciated that the invention is not limited to orthopaedic operations nor is it limited to any particular form or type of tissue or implant, but rather the systems and methods disclosed herein may also be utilised in procedures such as, for example, implanting medical devices or internal fixation Referring to FIG. 1 there is depicted a schematic flow diagram depicting the implant fit analysis process 10, segmented into the individual steps that comprise the process. The flow of information between these steps and the individual processing they may contain is explained in overview. Data collection 100 utilises a series of differing sensors in possibly alternating arrangements to produce varying amounts and types of data 100a based on a subject which may be tissue of the patient undergoing a procedure or an implant or prosthesis planned for implantation in the patient's body. Data processing 200 pre-processes and manipulates data 100a to generate processed data 201 with increased usability and evaluability. Data interpretation 300 analyses the processed data 200a and extracts useful information and structures based on the tissue and implant. Compatibility information 400 outlines the type of singular or combinatorial conclusions that may result from these interpretations 300a. This is complimented by passing the generated compatibility information through various models and algorithms adapted for predicting 500 the longevity and performance of the prosthetic implant. The models and algorithms utilised in prediction step 500 are initially generated through a machine learning or training process based on the mapping between historical compatibility information and the postoperative status of their patients. Once populated, new compatibility information 300a can be passed through wherein its identified indicators will be mapped to corresponding values relating to implantation durability, predicting the potential state of the connective interface 561. The resulting predictions 500a of implantation performance and durability are used to inform calculations in real time of possible corrective actions 600 that may be employed by the surgeon whilst the procedure is underway to improve the performance and durability predictions 500.

Figure 2:
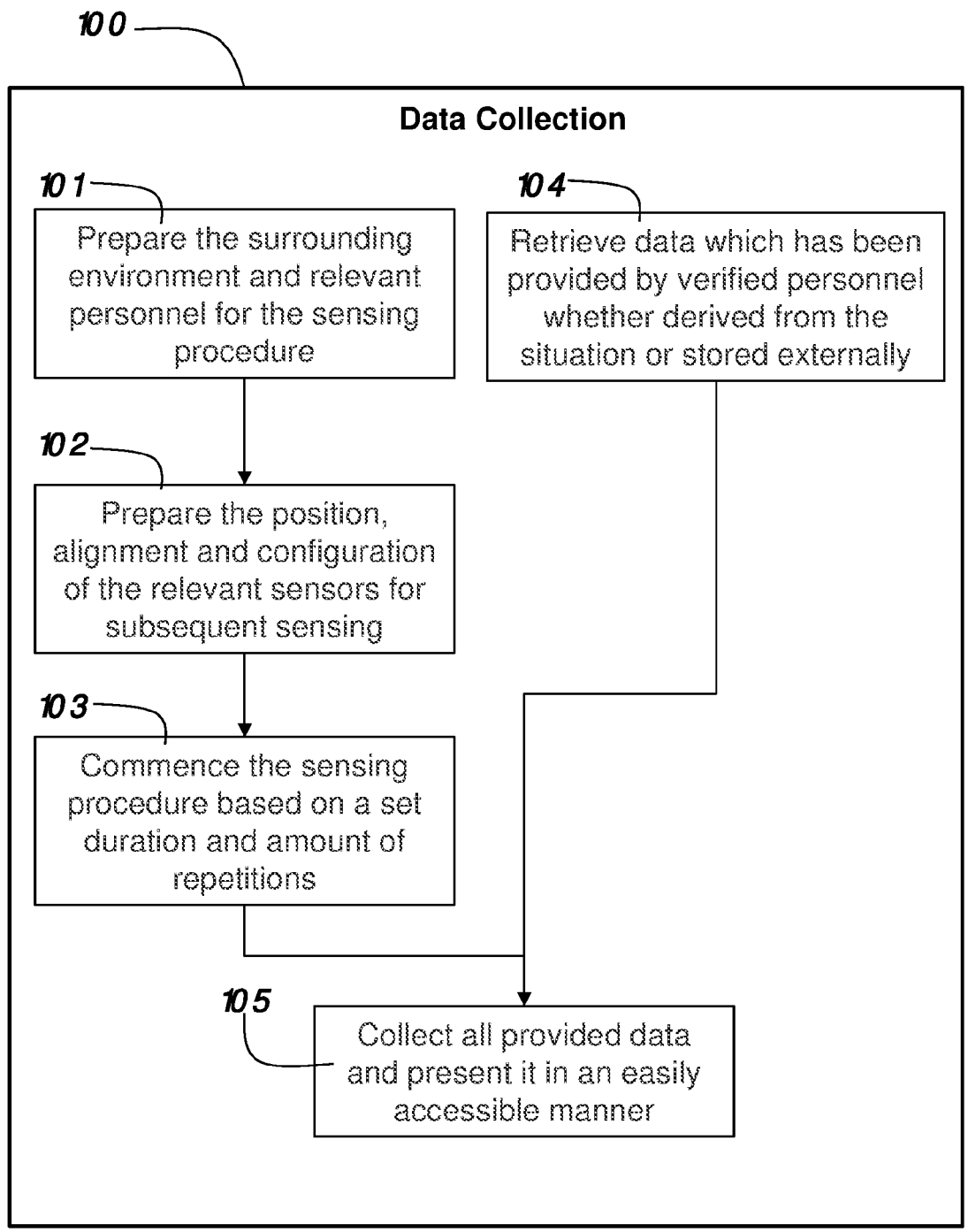
FIG. 2 is a detailed schematic flow diagram depicting the data sources and related procedures involved in the collection and accessibility of data as introduced in the exemplary data collection step in FIG. 1.

FIG. 2 depicts a detailed schematic diagram depicting an exemplary implementation of data collection step 100 of the implant fit analysis process 10 as depicted in FIG. 1. Data is collected through a series of sensors that may differ in terms of their type, quantity and arrangement across a multitude of possible embodiments. Sensors within these embodiments may act independently or as part of a system or collective of sensors where each cooperate in some fashion to increase the quality or amount of sensed data. Each sensor may be completely self-contained or may require additional devices or systems to handle all or some portion of the required processing.

The physical arrangement of sensors is advantageously made to surround the subject in a way that maximises sensing potential whilst resulting in the minimum amount of disturbance to the surrounding surgical environment. If the sensors exist as part of a system in a cooperative setup, then their arrangement should reflect this, such as sensing the subject from different angles to later combine the different perspectives together.

The sensors may be automated, manually triggered or controlled through some combination of the two depending on the particular system embodiment. In situations where a proper sensing environment must be created, it would be more opportune to control the sensors manually when this environment is presented. Manual control can be achieved through approaches which may include voice control, gesture controls and different forms of physical actuation, the latter of which is present within the particular embodiments described herein due to the precise control afforded to the surgeon or surgical assistant. Of course, in alternate embodiments, having the sensor work autonomously in conjunction with the calculation procedures to provide information without physical involvement from the surgeon or their assistants would be more advantageous. Variations to these approaches may also exist, such as, for example, the sensors being triggered automatically once they have perceived the required conditions e.g. the sensors may advantageously be continually operating in real time and, when a particular state Is perceived or observed, the sensor triggers a further operation within the system such as, for example, generating an alarm informing the surgeon that a condition has been obtained, or alternatively identifying undesirable parameters and triggering a calculation of corrective actions to overcome or correct the undesirable state.

In further embodiments, the sensors may be configured to sense in a periodic fashion since perceived changes may be unlikely to occur constantly, and their rate of sensing may be limited. In some embodiments, sensing may only need to occur once or may be continuous to provide a feed of information in as close to real-time as possible. In situations where snapshots or particular states are sensed, the provision of sensed data in a form of delayed time may be exercised as a number of states may be required to produce gainful data.

The selection of sensors and their configuration will be dependent on their sensed subjects. Sensing an implant and tissue will typically comprise at least one two-dimensional scanner (e.g. 2D optical sensor array), three-dimensional scanner (e.g. OCT, structured light sensor or laser line sensor), and hyperspectral or spectral sensors. These should be positioned to surround the implant or tissue at or near the implantation site with special focus placed on the areas where osteotomies will occur or have occurred, since these are the main areas that will participate in the implantation. Some of these sensors may operate in real-time and be periodically sensing provided that they have access to a clear line a sight. Other sensors may be excluded from direct operation until a point is reach where personnel prepare the theatre environment for ideal sensing conditions prior to reverting the environment after the sensing has occurred, for example removing sources of UV light from the environment so as to not interfere with an auto-fluorescence measurement sensor. In both cases it would be opportune for trusted personnel to be provided with the ability to manually trigger the sensors in addition to their autonomous operation. Manual triggers would typically comprise physical buttons or a touch screen control interface as to allow for efficient interactions.

Referring to FIG. 2, the surrounding environment and relevant personnel should be prepared 101 for any sensing procedures that may occur, depending on the sensors that are in use. This may, in particular embodiments, involve implicit preparation of the environment to ensure or increase the probability of optimal conditions occurring and temporary explicit modification of the environment if the involved sensors cannot sense efficiently during typical conditions. Such modifications may comprise having the personnel move any obstructing equipment and adjust any environment conditions such as lighting. Particular embodiments will normally require implicit preparation and some element of explicit preparation as would be appreciated by the skilled addressee. As orthopaedic surgery is generally time-constrained from both a monetary and medical perspective, reliance on periodic sensors that work around the typical operating environment of the surgical procedure is more advantageous than those which require constant changes to the setting and disruptions to the normal surgical procedure, although this occurring a small number of times during a procedure may be advantageous for significantly improving the surgical outcomes with minimal cost to the disruption of the surgical procedure itself.

The configuration of sensors are prepared 102 with consideration to any sensing procedures that may occur during the surgical procedure, provided the environment is in such a way that allows this to be possible or at least efficient. This may involve changing the position, alignment and orientation of sensors both independently and in relation to each other. Additional equipment such as stands or platforms may be necessary for these changes. In particular embodiments, the sensors will already be located in an optimised configuration as part of a pre-constructed system or platform. When the opportunity arises, the system as a whole can be moved into place in a relatively small time-frame, reducing environmental impact and disruption to the surgical procedure. After preparation 101, 102 has occurred, the sensing procedure can commence 103.

Sensing 103 is undertaken based on a set duration which determines the number of repetitions possible based on the particular sensor(s) utilised in the particular embodiment. In embodiments that require the environment and sensor configuration to be adjusted for optimal sensing conditions, these parameters are likely to be constrained by their setting. During orthopaedic surgery, this duration is likely to be only a few minutes as time is crucial for its success, meaning that only a couple hundred sensing repetitions is likely possible. In embodiments that allow for passive sensors, the duration may be dependent on the total lifetime of the subject being sensed or the actions performed in relation to it, with the repetitions being determined similarly. After sensing has completed, the preparatory measures 101, 102 implemented prior may be reverted if necessary.

Data may also be collected directly through provisions from verified personnel or systems 104 which may include documents, records and databases which may be either derived from the surgical procedure or sourced from external storage repositories such as current or historical patient records. In a particular embodiment, such external sources may comprise any resources that could provide additional information on the patient or the operation that they are undergoing, such as, for example, patient records, medical records and historical operation or surgery data.

All data sensed and provided will be collected and presented in an easily accessible manner 105 as required by the necessary processing in step 200. Data collection may preferably involve the extraction of data in whichever format is deemed the most usable, generally determined by the sensor it originated from. Sensed data obtained from the plurality of sensors may initially appear in a raw format which must be converted into data of a form that is readily accessible to data processing step 200, such that meaningful calculations can be performed on the collected data and from which, meaningful analysis and predictions can be derived. Such formatting of the raw sensor data may advantageously be performed by an external control unit. Similarly, provided data may appear in a form that cannot be easily accessed, such as paper, which requires manual input into a digital system to make it accessible to the data processing system. In a particular embodiment, all data would advantageously be stored in the same way so that they can be accessed in the same way. This method of storage would ideally be the random access memory (RAM) of a central system, although a solid state drive or hard disk may be used instead depending on the raw amount of data and processing speed required for data processing. In alternate embodiments, a database may be used to store and access this data. Such a database, may use strict storage and access guidelines as imposed by SQL or be more flexible and scalable using technology such as NoSQL.

Figure 3:
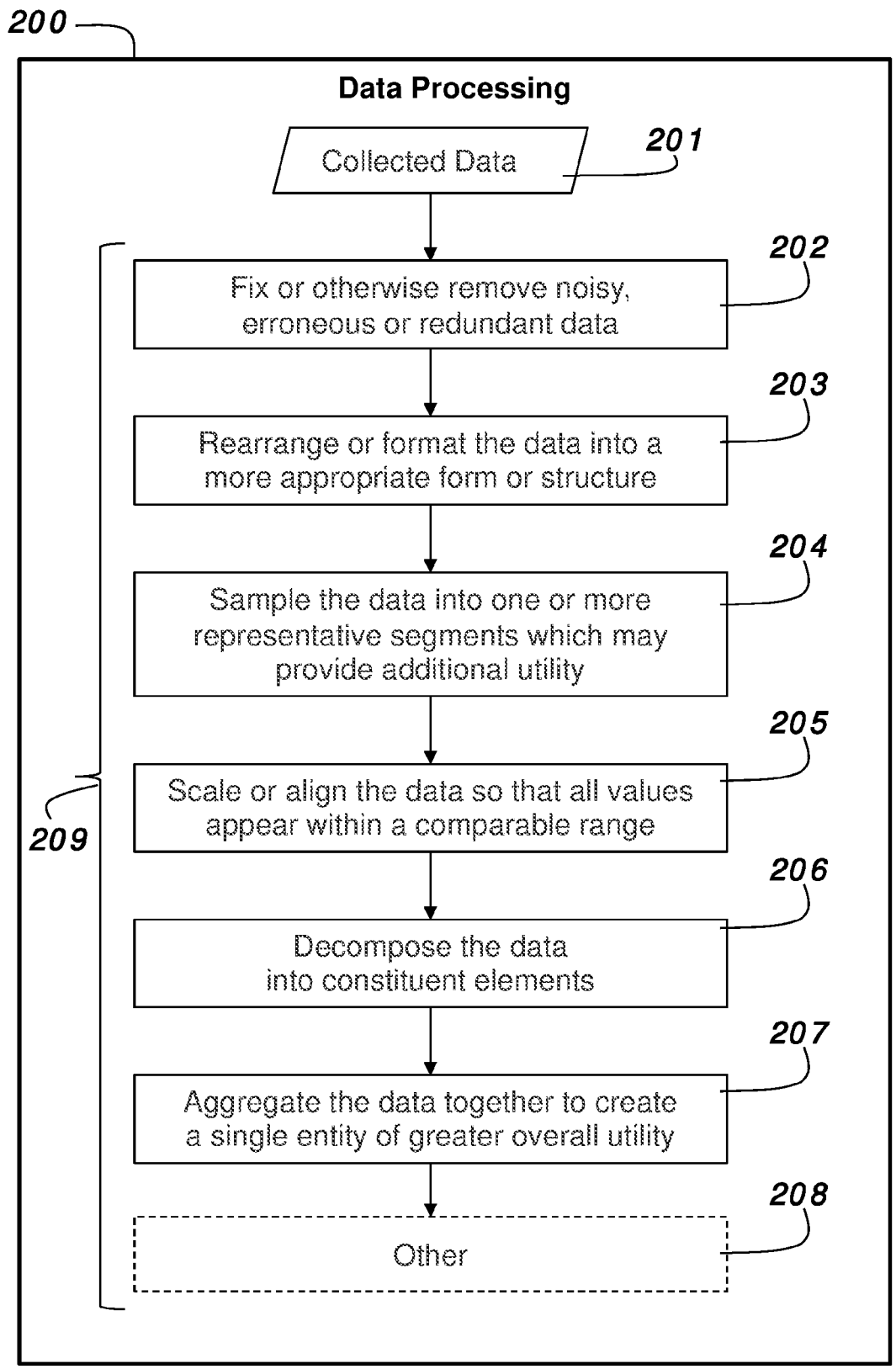
FIG. 3 is a detailed schematic flow diagram depicting the processes and manipulations involved in the preparation of data as introduced in the exemplary data processing step in FIG. 1.

FIG. 3 shows a detailed schematic diagram depicting an exemplary data processing step 200 of the implant fit analysis process 10 as depicted in FIG. 1. Data processing involves the preparation and manipulation of data to transform it into a form of greater utility, generally in terms of both its usability and evaluability.

Collected data 201 will typically be in a somewhat raw format which may contain noise, errors or redundancy. If data containing such flaws is used un-processed during normal processing, redundant calculations, inconsistencies or incorrect results may occur. These must therefore be fixed or removed 202 depending on their type and severity.

Noisy data may be defined as data that is partially correct but contains other portions that are corrupt or in error. The proportion between the correct data and that which is in error is an indicator about the type of actions that can be taken in response to it. If only a small amount is in error, then it may be possible to fix this amount based on the correct data, or it could be removed provided that the remaining data provides sufficient benefit in its reduced form. If the amount of incorrect data is large however, then removing the data as a whole is likely the only option.

Erroneous data may be defined as data that is wrong and contains values which cannot possibility exist either through the medium that created it or in relation to surrounding data. Erroneous data cannot be fixed in most scenarios as it typically has no relation to the value that it should have been and is therefore usually removed.

Redundant data may be defined as data which, although not in error, does not add any additional value or benefit to the data set as a whole and only serves to increase its volume and introduce inconsistencies. Redundant data cannot be fixed as it is technically correct and is therefore usually removed or ignored instead.

Removing or fixing data is highly dependent on the origin and format of the data and the severity of the errors in question. Removal is relatively straightforward depending on the format but will leave the remaining data in a reduced state. The data will remain valid in some cases, but others may require additional modifications to achieve this. This may entail combining the remaining data with other sets of reduced data to create complete sets or replacing the data with dummy data that will not affect the end result. The fixing of data in comparison is more difficult and requires knowledge about the expected structure to determine what is missing or wrong so that it can be rectified. Techniques to achieve this are highly dependent on the data itself and may not even be possible. In a particular embodiment, all redundancy and errors will be directly removed, whist any noise will be fixed if additional benefit can be discerned.

Collected data 201 will typically need to be rearranged and formatted to increase access efficiency and make its storage more logical in terms of processing 203. This is because its initial form will likely be based on the ordering and format of its origin, such as a specific sensor, system or set of personnel, which is suboptimal for manipulation.

In a particular embodiment, rearrangement consists of gathering data from multiple avenues and sorting them in such a way that, despite being from different sources, data with similarities or of which can be used in similar ways will be grouped together. This will allow data to be searched based on properties that they may have and allow related data to be found within the same vicinity. Formatting will consist of various structures that increase the accessibility of different groupings in terms of the types of data that may be manipulated simultaneously and subsequently. Other embodiments may have differing approaches to formatting and arrangement depending on their application.

Collected data 201 may be sampled 204 to create different segments which provide additional utility in comparison to operating based on the data as a whole. Sampling 204 may consist of reducing the data pool into one that is more representative, such that although it may contain a smaller amount of data, the value or benefit that the data produces overall will either be the same or compare favourably to the full data set. It may also consist of splitting or dividing the data pool into individual segments where each segment has a different purpose, usually defined by the way it may be used. This could include separate segments for averaging, testing, training and/or validation in accordance with requirements.

In a particular embodiment, the entire data pool may initially be reduced into a more representative sample so that computational load can be decreased, and the remaining data can be more readily interpretable. This reduced sample will then be split into a plurality of different segments.

In a particular embodiment, this reduced sample may be split into four distinct segments where that division of the data pool would result in the eventual best results over any other division.

The first two larger segments will be used as the main sources of data, with all related processing performed with the intent of drawing usable information. The results of each individual segment can then be compared or averaged to ensure that results seen by processing of one of the segments is a result of processing and not inherent traits within the data itself or because of any other inconsistencies. This comparison may be similarly performed between the individual segments and some resulting combination of them to monitor the impact that additional or different data has on accuracy or derivable information.

The remaining smaller segments may be used to test the performance and validity of the larger segments. This will mainly be in conjunction with machine learning data processing techniques, data science and mathematical algorithms or methods as will be appreciated by the skilled addressee to determine how accurate the calculations performed actually are and if they are capable of being performed on data they have not already seen.

Other embodiments may be realised which determine the split of the collected data based on the intended application and processing that will be performed on that data. It may be advantageous to use the data as a whole or use multiple sets of data and average out a solution. Similar combinations or approaches may also exist for data segments that will not participate directly in data generation, such as testing and validation segments, although these may not necessarily exist.

Collected data 201 may need to be scaled or aligned so that it is easily comparable 205. This is because values provided from different sources or even the same source may differ drastically in range even though they may represent or describe the same instance. By changing the range to a common point, comparisons may become easier and processing algorithms or methods with such requirements become viable.

In a particular embodiment, this will be performed for all values originating from the same source during a single sensing run and may also be performed for all sensing runs depending on how different the context and environment is for each of them. Data from different sources will likely not be scaled together as their representations may be too different and the processing required to result in a comparable form may reduce their overall utility. Other embodiments will likely scale depending on the sensors used, the intended application of the sensed data and the processing of that data.

Collected data 201 may be reduced, split or decomposed 206 into their constituent elements, or individual elements which comprise the data to identify and use only the main beneficial elements as opposed to all of them.

This decomposition will reduce the amount of redundancy present and subsequently decrease the computational load as the remaining elements will no longer be processed. This is under the assumption however that the constituent elements hold either the vast majority of utility or at least enough that any small amount of utility held by the remaining data will be of no consequence or of less benefit than the decreased computations.

Selected constituent elements may hold relevance to a particular application or form of processing whilst the remaining data either cannot be used or will produce no meaningful information in doing so. This is especially apparent in machine learning, data science and mathematical algorithms or methods as constituent elements are typically good indicators when used in various complex mapping procedures.

In a particular embodiment, data will be decomposed into their constituent elements if a specific element or series of elements will better represent the data in comparison to the entire data set as a whole. They will also be used in conjunction with machine learning, data science and machine learning algorithms or methods to increase their predictive accuracy, especially in scenarios where constituent elements are comparatively more precise. Other embodiments will likely decompose data into their constituent elements to some degree, typically with the same reasoning as the embodiments discussed previously but possibly in different quantities and scenarios.

Collected data 201 and possibly constituent elements may be aggregated together 207 to create an individual entity that has more utility in comparison to the individual data or elements that it is comprised of. By reducing the data available to a singular expression, this also reduces the amount of redundant computations involved.

Aggregation approaches 207 are largely dependent on the application, the type and expression of data, and the forms of processing their results will be used with. Simplistic approaches may involve, for example, averaging the involved data together whilst more complex ones may involve, for example, providing a weighting to each individual element and performing a procedure that processes and combines them based on these weightings. As the amount of information relating to the context of the data and application increases, the complexity and utility granted by these aggregation approaches may do so as well.

In a particular embodiment, data or constituent elements may be aggregated 207 together provided that this aggregation grants more benefit than would otherwise be possible individually. It may be performed for all sources of data but will likely be restricted to data of similar origin as different aggregation algorithms may require some amount of similarity to be productive. Other embodiments will likely aggregate data in a similar manner, with their dependencies determining how and in what degree this will occur.

Other processing methods 208 as would be appreciated by the skilled addressee may optionally be utilised 208 in addition to those mentioned above in accordance with requirements. The ordering and existence of the data processing steps employed in a particular embodiment may not necessarily reflect the ordering and existence of the approaches 209 described herein. For example, in accordance with requirements of the form of the collected data, the particular data processing steps utilised for a particular application may comprise any useful selection of the available data processing step 209 and such selected steps may be applied in any suitable order.

Figure 4:
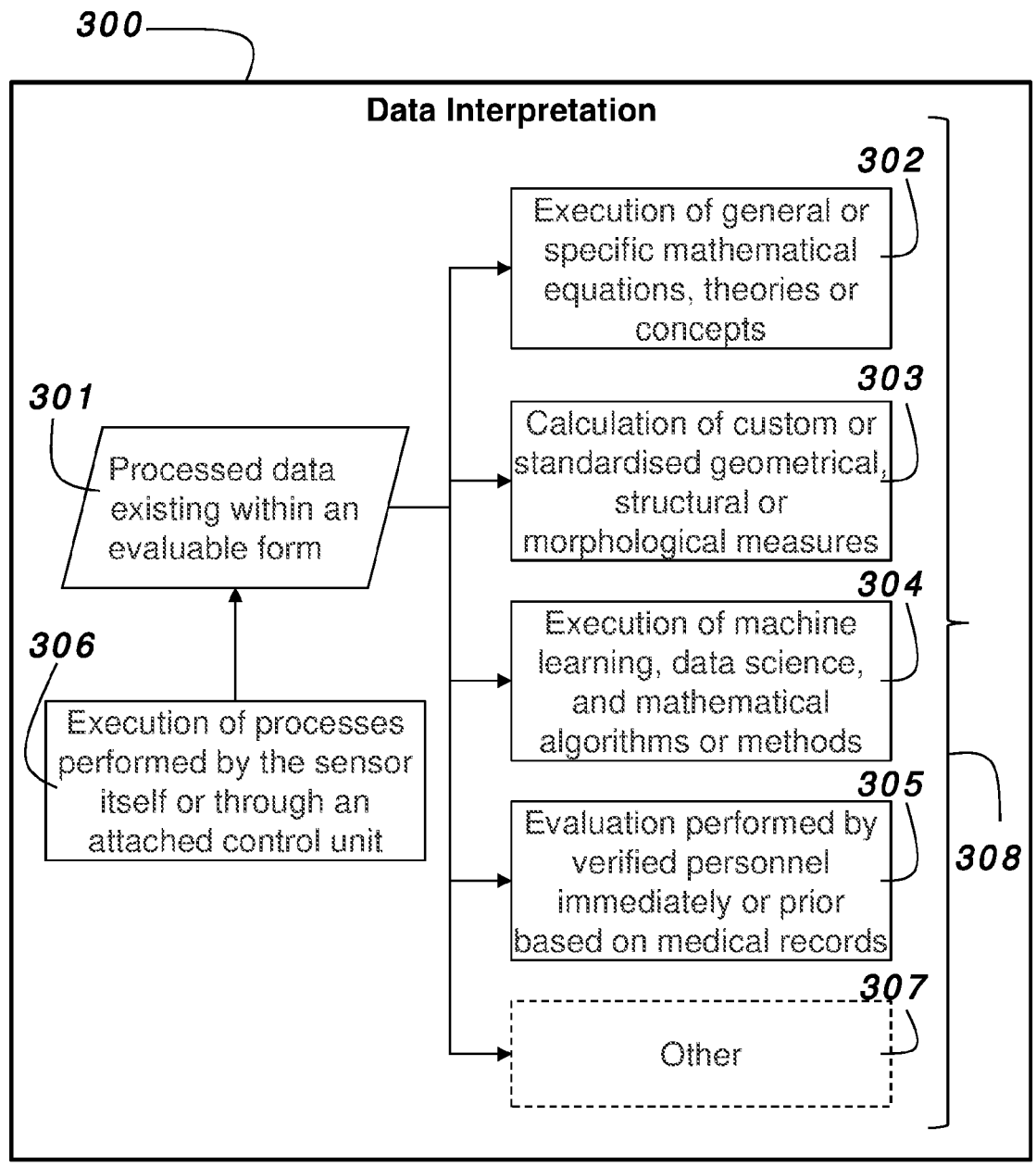
FIG. 4 is a detailed schematic flow diagram depicting the algorithms, methods and calculations involved in the analysis of processed data as introduced in the exemplary data interpretation step in FIG. 1.

Turning now to FIG. 4, there is shown a detailed schematic diagram depicting an exemplary data interpretation step 300 of the implant fit analysis process 10 as depicted in FIG. 1. Data interpretation involves analysing processed data in an evaluable form 301 to generate information and statistics which is able to describe various characteristics based on that data.

Measurements defined by mathematical or statistical equations, theories or concepts may be calculated 302 to generate summarised information based on evaluable processed data 301 obtained from data processing process 200. These calculations will typically produce a single value that can describe a specific property or series of properties relating to the data that is used. This may include measurements such as the mean, standard deviation and variance of the data. These calculations should be performed on sets or samples of processed data which contain some degree of similarity, as if the data is completely independent, then the results will reflect this independency which may have little practical use.

Whilst the measurements themselves may not allow conclusions to be derived based solely on them, they have alternate utility in providing reinforcement for conclusions developed through other data interpretation approaches. This will likely be their main purpose, especially if the desired conclusions are rather complex.

In a particular embodiment, these calculations will be performed on all data samples, provided that they are similar enough to produce beneficial results, wherein this similarity may be based around their origins, their processing methods or their subjects. Other embodiments will likely perform these calculations similarly, although the data sets they use as input may differ based on their application.

Custom, specialised or standardised measures may be calculated 303 to generate information based on evaluable processed data 301. These calculations are typically based around the data itself and its expression, which is in turn closely related to its origins or more specifically the particular sensor which generated the data (assuming that the data was indeed generated by a sensor). This means that they are largely dependent on the application and may not necessarily be included in all embodiments, although if an embodiment does have the conditions and capability required to utilise them, it will likely do so. Such calculations may include those based on image colouring, acoustic signal wavelengths or positional readings.

Custom or specialised calculations are those which can only be applied to a specific situation and may have been created or modified especially for this purpose. Standardised measures in comparison are those created and maintained by a standards organisation which have the same meaning and equation irrespective of their subject or the data that they are provided with.

In particular embodiments, both custom and standardised measures are used where a benefit can be drawn from each. Custom measurements will mainly consist of those that relate directly to medical operations or surgery, such as determining the mechanical axis for a particular knee joint. Standardised measures will be mainly derived from the International Standards Organisation (ISO) and may include those based on geometrical, structural and morphological measures. This will allow attributes including surface flatness and roughness to be calculated in a comparable way. Other embodiments will likely make use of both provided they exist in a situation that will allow this.

The execution of machine learning, data science and mathematical algorithms or methods 304 may be used to generate predictions based on evaluable processed data 301. These predictions will typically detail some property of the data that cannot be determinatively discerned to varying degrees of accuracy.

Predictive algorithms and methods come in many different forms, separated by their usage requirements. The amount and quality of data provided to them determines their level of accuracy and therefore usability. Ideally, each set of provided data should be reasonably independent and have a large enough size such that the predictive algorithm or method can learn why the data exists in the set that it does and any edge cases that may be present.

Data passed to these predictive algorithms or methods typically cannot be used raw and must be processed in specific ways based on the form of predictive analysis. This may involve transforming the data into a more accessible form prior to transforming it again into a more evaluable form that is increasingly singular and easier to work with, often consisting of specific constituent elements.

In particular embodiments, supervised algorithms or methods will be the main form of predictive analysis. These work by mapping input data to a value or set of values using indicators determined through previous historical data. This process involves two main steps, training and execution.

Training consists of providing the algorithm or method with large amounts of data along with the value or set of values that each should correspond to. The algorithm or method will look through the data and the corresponding values to discern which indicators in the data result in which value. A computational structure is created from this mapping which accepts data as input and return its corresponding values based on the indicators that it contains as output.

Execution consists of passing new data to this structure/model, which will extract the relevant indicators from it and then return the corresponding value or set of values which may, for example comprise a computed value representative of a numerical predication of the implantation performance and longevity prediction of the orthopaedic implant.

Evaluation of evaluable processed data 301 may be performed manually either by verified personnel or through prior documentation 305. In a particular embodiment, this would consist of a surgeon or other medical practitioner looking at the data as it is generated and providing conclusions and insight based on their experiences, which may be used to train the computational models used for analysing the data Similar conclusions may also be provided preoperatively based on medical records which can inform the various processes and approaches described herein.

Data analysis may be performed to varying degrees by the sensor itself or through an attached control unit 306. This will likely be quite data dependent, such that the provided analysis may be based around attributes or properties that that particular sensor is specifically engineered for.

The results of this internal analysis may produce benefit independently or may be used as additional data that can be included as evaluable processed data 301 to assist with and be processed by subsequent interpretation approaches. In particular embodiments, both of these approaches may be used as it will be assumed that internal sensor processing may produce information that is beneficial independently and as part of the larger data pool.

Other interpretation approaches may exist 307 in addition to those mentioned above. The ordering and existence of these approaches may not necessarily reflect the ordering and existence of the approaches herein 308.

Figure 5:
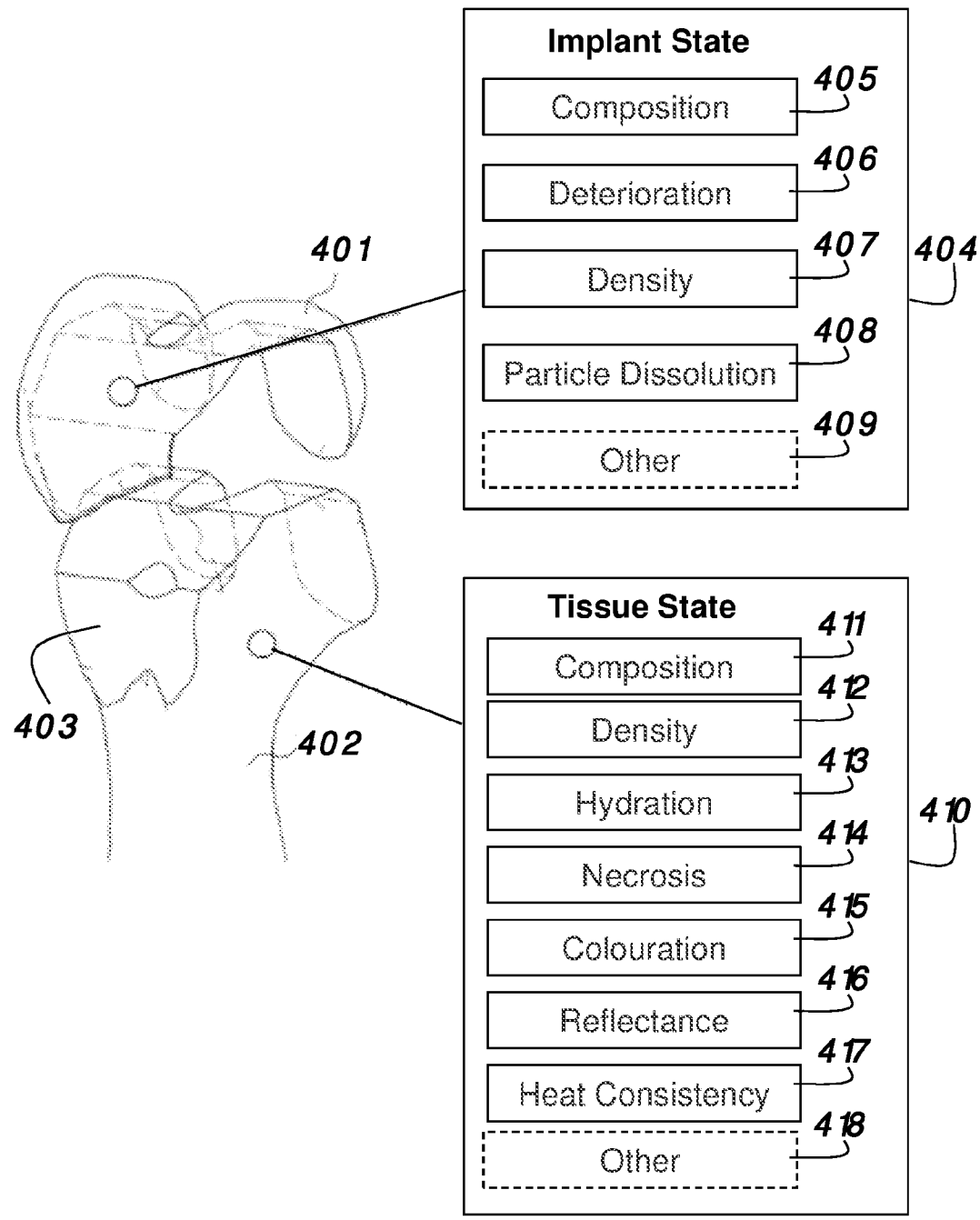
FIG. 5 illustrates generally possible properties describing state which may exist for the implant and hard tissue.

FIG. 5 illustrates an example implant and tissue interface with the state of each being outlined as part of the depiction of an exemplary compatibility information generation step 400 of the implant fit analysis process 10 as depicted in FIG. 1. The state refers to the condition of the implant 401 or tissue 402 at a particular given moment in time, which is typically determined intraoperatively. It may be interpreted as a series of properties that can be used to describe specific parts or areas of itself.

Implant state 404 comprises a series of descriptors that provide information relating to the build and integrity of the physical implant. Composition 405 describes the type of materials that the implant may be composed of. Specific materials may degrade faster, be more vulnerable to impacts or cause reactions when used against some types of tissue. Deterioration 406 may describe both the current state of the implant and the rate at which it will naturally degrade when inserted. If an implant has already begun to degrade or has an accelerated rate of degradation, then inserting it would likely result in reduced longevity and performance for the patient. Density 407 may describe how compact the particles existing within the implant are and will provide an indication of its hardness and how well it may react to external trauma. Particle dissolution 408 is the rate that material particles may be expelled from the implant and how this rate changes over time. These particles will generally be seen as foreign bodies within a patient and may prompt an internal response that could be damaging to the connective interface between the implant and tissue.

Tissue state 410 comprises a series of descriptors that provide information relating to tissue health of the patient at the implant site. Composition 411 describes the types of minerals that may comprise the tissue. The different minerals and their abundances generally make a reliable indicator as to the health and age of a specific tissue and notably differ when variations to these properties are present. This is further reinforced by tissue density 412 which defines how tightly packed these minerals, or at least specific minerals, are in relation to each other. Hydration 413 may describe the water content existing within the tissue that can be useful in measuring the impact of any prior osteotomies and timing implant insertion. Necrosis 414 is the death of tissue cells which may have been caused by the method of osteotomy or internal issues within the body. Colouration 415 is the particular colour that the tissue exhibits wherein any variations typically cannot be discerned without advanced visual sensors. Reflectance 416 is how much and what colours the tissue can actively reflect. Heat consistency 417 is the temperature of the tissue and how this is distributed across it. Measuring heat consistency is often a good way to monitor how the tissue is being affected when performing osteotomies and other operations.

These state descriptors will be generated based on interpretation procedures 308 detailed in FIG. 4 and may include or be influenced by any patient specific conditions or structures. Generating all descriptors may not be possible depending on the sources of data that are available and the types of descriptions that may be useful to a particular application. The implant state descriptors 404 and tissue state descriptors 410 explored herein are those which may be useful in determining the compatibility between an implant and tissue as part of a particular embodiment, although other implant 409 and other tissue 418 state descriptors may exist as would be appreciated by the skilled addressee.

Figure 6:
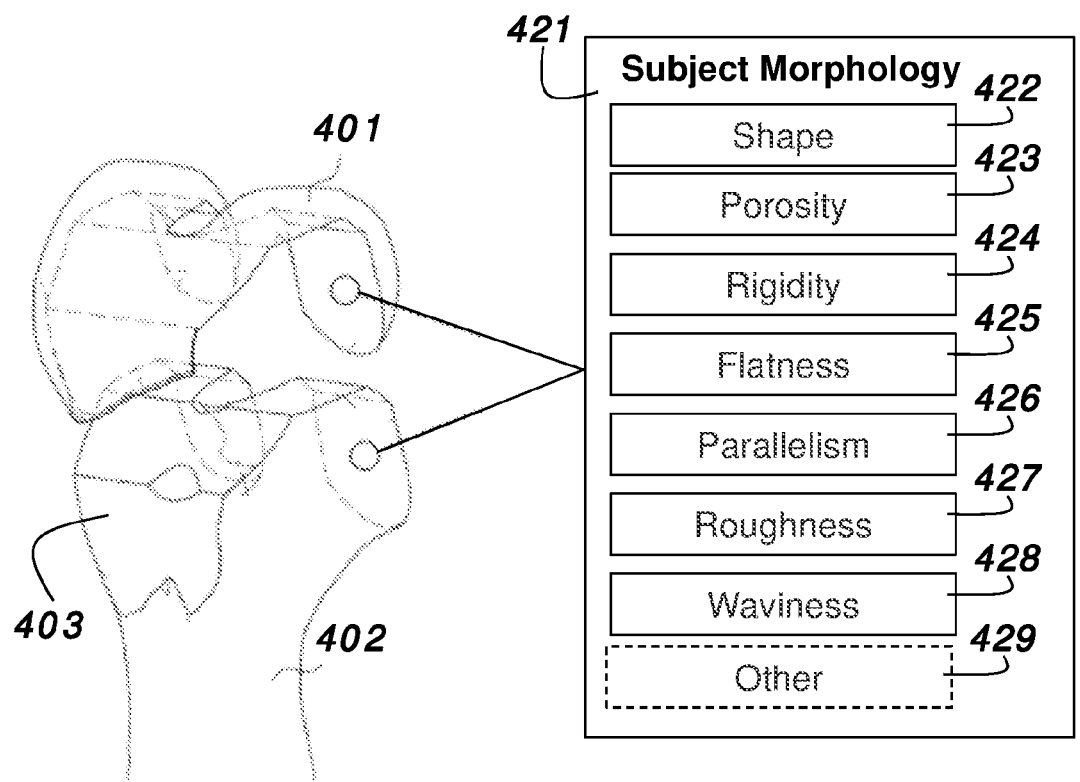
FIG. 6 illustrates generally possible properties describing morphology which may exist for both the implant and hard tissue.

FIG. 6 illustrates an example implant and tissue interface with the morphology of each (i.e. the implant prosthetic 401 and the patient tissue 402] being outlined as part of the depiction of an exemplary compatibility information generation step 400 of the implant fit analysis process 10 as depicted in FIG. 1. The morphology refers to the form, shape or structure of the implant 401 and tissue 402, which is typically determined intraoperatively. It may be interpreted as a series of properties that can be used to describe specific parts or areas of itself.

Implant and tissue morphology 421 comprises a series of descriptors that provide information relating to their form, shape and structure. Shape 422 describes a geometrical figure typically in terms of its contours and mass. This descriptor is the basic starting point in determining the morphological compatibility between the implant and tissue as it will define whether or not the two can actually fit together. If the shape of either causes collision when joined, insertion may not necessarily be possible. In particular embodiments, the distances between the contours of each shape during insertion should be as minimal as possible. Porosity 423 describes how many small physical holes an entity may contain and the size and distribution of these holes. Rigidity 424 describes how fixed a specific entity is in terms of its inability to be moved or bent into a different shape. Although not necessarily important when used with singular entities, it may provide a measure of connective potential and fault tolerance when used with two or more.

Flatness 425 describes the deviation between the height of peaks existing on a particular surface and their average height. If this deviation is relatively large, then it can be assumed that the surface has a low degree of flatness with the opposite being true if it is relatively small. This definition is often dependent on the context and application however as a surface that has an uneven distribution but one that allows an object to rest flush upon it may still be considered flat. In a particular embodiment, it will be defined according to the ISO standards. This states that a surface may be deemed flat if the peaks and troughs existing within it do not exceed a predefined limit. This limit will likely be set to 0.3 mm which is the maximum gap required to reduce postoperative issues such as aseptic loosening. All surfaces of the tissue 402 may need to be flat in order to comply with the surfaces of the implant 401.

Parallelism 426 describes the deviation and distribution of peak heights between one surface and another. If their peak heights and distributions are similar, then it can be assumed that both are parallel. This definition is also often dependent on the context and application in which it is used. In particular embodiments, it will be defined according to the ISO standards. This states that a surface may be deemed parallel to a particular datum or other surface if the peaks and troughs of the surface, according to its current angle, does not exceed a predefined limit. All corresponding surfaces between the implant 401 and the tissue 402 may need to be parallel to ensure maximum contact. This will likely mean that the predefined limit should be minimal.

Roughness 427 describes the routine irregularities affecting the peaks and troughs of a surface usually resulting from a particular machining process or natural biological growth. Waviness 428 in comparison relates to abnormal irregularities instead and tends to be spaced further or consists of longer wavelengths. It is generally considered as a broader form of roughness. This usually results from tool deflections, vibrations or heat treatment. In particular embodiments, the roughness and waviness of the tissue may advantageously be manipulated so that it matches that of the implant to encourage osseointegration.

These morphology descriptors are normally generated based on interpretation procedures 308 detailed in FIG. 4 and may include or be influenced by any patient specific conditions or structures. Generating all descriptors may not be possible depending on the sources of data that are available and the types of descriptions that may be useful to a particular application. The descriptors 421 explored herein are those which may be useful in determining the compatibility between an implant and tissue as part of a particular embodiment, although other implant and tissue morphology descriptors may exist 429.

Figure 7:
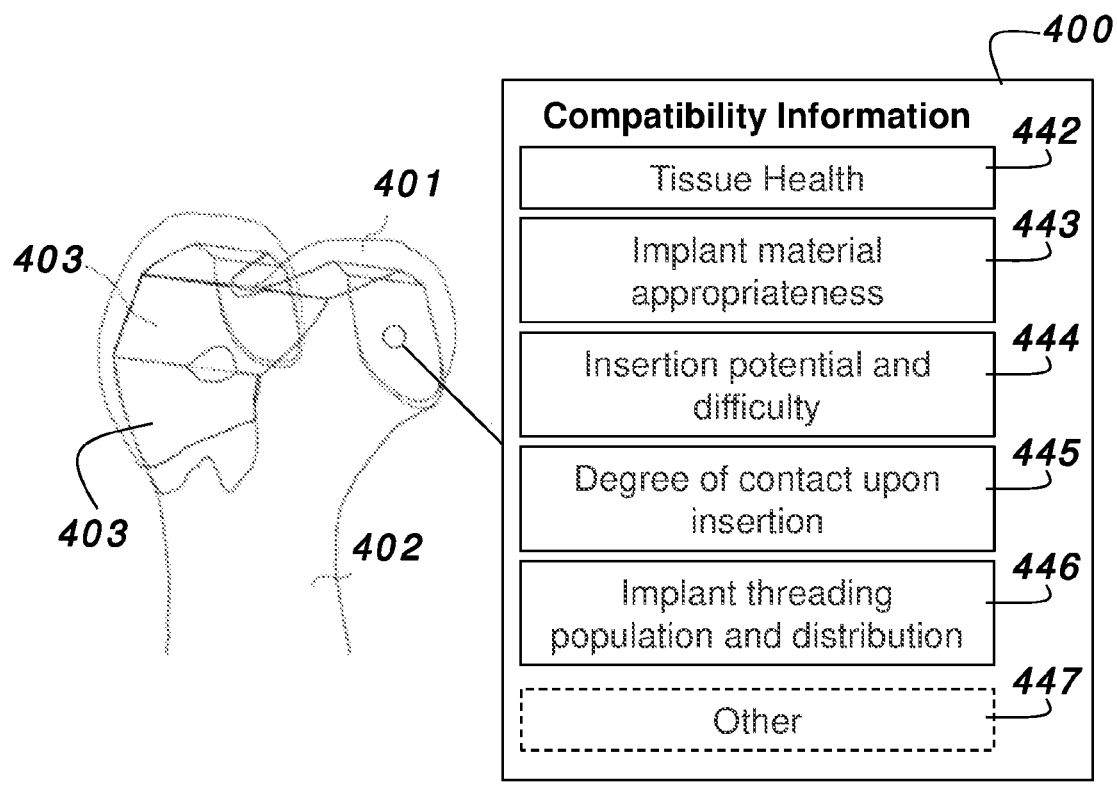
FIG. 7 illustrates generally possible properties describing the quality of the potential connective interface derivable from state and morphology information relating to a specific implant and hard tissue.

FIG. 7 illustrates an example implant and tissue connective interface with its associated compatibility information being outlined as part of the depiction of an exemplary compatibility information generation step 400 of the implant fit analysis process 10 as depicted in FIG. 1. Compatibility information 400 refers to properties, characteristics and attributes relating to the quality of the connective interface 403 existing between a particular implant 401 and tissue 402.

Tissue health 442 comprises the tissue state 410 of patient's tissue 402 and how this will be affected by both the implantation procedure and the implant itself. This is split into two different considerations. The first involves whether or not the tissue will be able to exist within a connective interface 403. If the tissue health has deteriorated too much, which may be the case for some patients, then a replacement procedure may not be beneficial or recommended. This may also be the case if the tissue health will not allow it to properly participate in the interface, such as if its potential for osseointegration is relatively low and it may react negatively to various types of fixatives. The second consideration is how it will exist in tandem with the implant, or more-so, how appropriate the material of the implant may be.

Implant material appropriateness 443 comprises the state 404 of the implant 401 and involves two main areas which are closely connected:

What the implant may affect, e.g. if the implant consists of a material that is known to be relatively brittle and will therefore have a large amount of particle dissolution, an internal response is likely, which could result in damage to the connective interface. The same may occur if the material triggers a natural reaction, such as an allergic response, through its contact with the tissue.

How the implant itself may be affected, e.g. regular stress based on the actions of the patient is to be expected depending on the replaced joint. However, if this stress becomes too great or too frequent then trauma may occur. This may make the implant increasingly susceptible to further stress and may cause or exacerbate issues relating to its connective interface. This information in conjunction with tissue health will provide insight into how the tissue and implant will interact as part of the connective interface 403.

Implant Insertion potential and the difficulty involved 444 comprises comparing the morphology of the implant and tissue 421 after adequate preparations to determine the possibility of connecting them. This will typically involve one of two different scenarios. The first scenario is that the required osteotomies have not been performed or are not at the depth required, making insertion unlikely since the tissue will be too large. The second scenario is if the required osteotomies have been performed and have exceeded the required depth. This means that the distance between the contours of the tissue and the implant will be quite large, so whilst insertion will be relatively easy, the resulting fit will be of low quality. In particular embodiments, a result falling between these two scenarios may be achieved such that the distance between the contours of the implant and tissue is minimal.

The degree of contact upon insertion 445 details the quality of the fit or connective interface existing between the implant and tissue. If there is a small degree of contact or if the contact is distributed in uneven or irregular ways, then the resulting connective interface may be considered poor. This is because the less contact that exists across a fit, the more difficult it will be for the tissue to successfully integrate into the implant. Instead, only sections will be properly attached which means that when the interface is under stress, these sections will be disproportionally affected and wear quicker. This effect is not as pronounced when a fixative is used in the connective interface but is still important as if not all areas of the implant make contact with the fixative then the same issues will occur. Comparatively, if there is a large degree of contact and this contact has an even distribution, then the resulting connective interface may be considered high quality. This is the desired result for the particular embodiments discussed above.

Implant threading population and distribution details how well the surface of the tissue has been moulded to accept the implant threading in an advantageous manner 446. Implant threading is a particular coating across the surface of an implant that is meant to encourage osseointegration of the tissue. This will likely consist of the proportion and distribution of peaks and troughs that match and are inserted into the corresponding troughs and peaks of the implant threading respectively. This may be based on the morphology of the threading itself as opposed to any specific implant as the threading pattern will likely be independent to the implant. In particular embodiments, the surface of the tissue will favourably match the threading of the implant so that a greater level of osseointegration may be achieved.

This compatibility information will be generated based on tissue and implant properties 404, 410, 421 as detailed in FIGS. 5 and 6, and on interpretation procedures 308 detailed in FIG. 4, and may include or be influenced by any patient specific conditions or physical structures. Generating them all may not be possible depending on the data sources that are available and the types that may be useful to a particular application. The compatibility information 400 explored herein are those that may be useful in defining the compatibility between an implant and tissue as part of a particular embodiment, although other compatibility information may exist 447.

Figure 8:
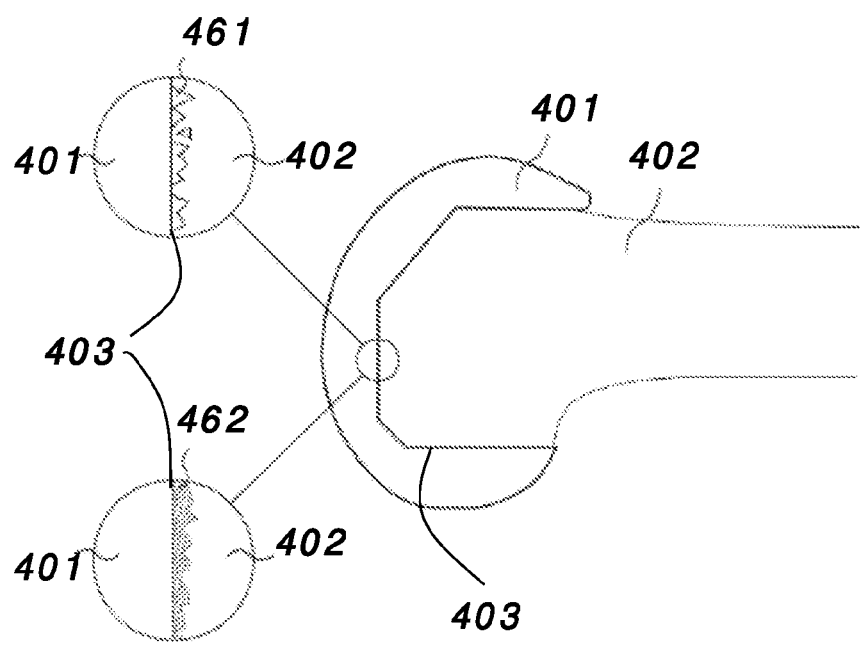
FIG. 8 illustrates generally the effect of implant insertion on the specific hard tissue and any existent fixative.

FIG. 8 illustrates an example implant and tissue connective interface with the impact of the insertion process being outlined as part of the depiction of an exemplary compatibility information generation step 400 of the implant fit analysis process 10 as depicted in FIG. 1.

Inserting an implant onto tissue intraoperatively is no easy task. It typically requires a great deal of physical force from the surgeon or other participating personnel. This is especially apparent when the tissue has had multiple osteotomy operations to ensure that its post-osteotomy morphology (i.e. at connective interface 403) is as appropriate for the implant as possible, leaving only a minute gap for insertion. According to some literature, this is to be interpreted as each point of the tissue 402 being a maximum of 0.3 mm away from the implant 401.

Accordingly, issues or damage (to either the tissue or the implant) may be caused to the tissue 402 and implant 401 during the implant insertion process, although the potential for damaging the implant is significantly less. This typically entails disfiguring or breaking various post-osteotomy detailing along the surface of the tissue e.g. at connective interface 403. For procedures based on osseointegration, this will consist of breaking the peaks and disrupting their distribution 461, resulting in an imperfect interface surface as shown in FIG. 8. For procedures based on a fixative, this will consist of spreading the fixative irregularly so that some areas 462 may have more in comparison to others.

Although this may not be as detrimental to fixative-based procedures, for procedures that rely on osseointegration, this process is essentially changing the morphology of the tissue. It may be possible that, based on these changes, the new morphology produces a connective interface of lesser quality. This may create or increase the probability of some postoperative issues occurring.

The degree of peak breakage or fixative displacement may be analysed and predicted prior to insertion based on previously compiled compatibility information 400 as detailed in FIG. 7. This evaluation may be used to inform the generation of other compatibility information and may prompt the regeneration or recalculation of those that may already exist. It is to be performed as many times as deemed necessary in accordance with requirements, for example to maximise the implantation performance and longevity prediction in step 500 of implant fit analysis process 10. In particular embodiments, this will be interpreted as each time the generated compatibility information surrounding the implant, tissue or their resulting connective interface is changed.

Figure 9A:
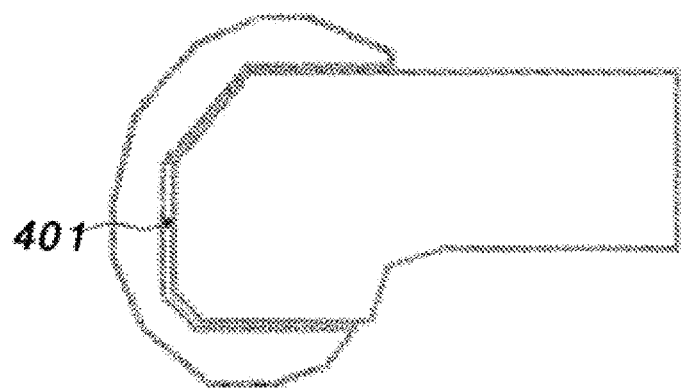
FIG. 9A, FIG. 9B, and FIG. 9C, illustrates generally the internalised virtualisation of a calculated perfect connective interface and the properties which are used to derive related quality indicators based on an existing implant and hard tissue pair.
Figure 9B:
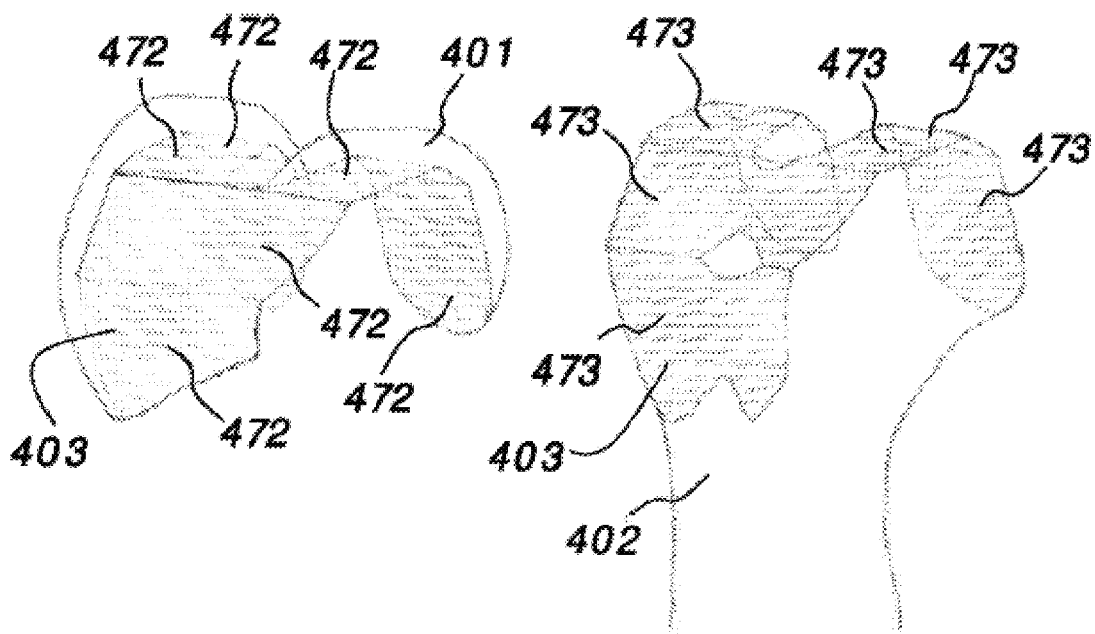
Figure 9C:
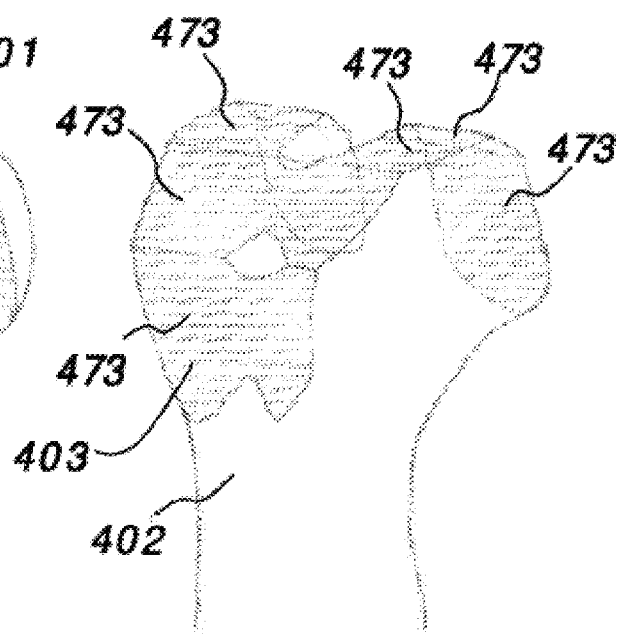

FIG. 9, including FIG. 9A, FIG. 9B, and FIG. 9C, illustrates a partially simulated implant 401, tissue 402 and resulting connective interface 403 to evaluate the ideal placement of the implant as part of the depiction of an exemplary compatibility information generation step 400 of the implant fit analysis process 10 as depicted in FIG. 1.

Placement may comprise many different measures and properties which may, for example, include the degree of contact between an implant 401 and tissue 402, the angle of the implant relative to the tissue and the stress distribution on the implant.

Virtualisations based on the morphology of the implant 472 and tissue 473 may be generated. The ideal placement 471 can then be derived from these individual visualisations with previously generated compatibility information 400 guiding this process. In particular embodiments, generation of the compatibility information may involve determining the maximum amount of contact possible between the implant and tissue, the most advantageous angle for the implant to be inserted in, the amount and likely distribution of any breakages and/or the spreading or displacement of any added fixative.

The result of physically inserting the implant onto the tissue can be compared to this ideal placement to determine how close they are together and what may need to change to minimise this difference. This may involve using various sensors or other measuring equipment to generate information based on the physical fit. This equipment may be general, purpose-specific or comprised of those used previously as detailed with reference to data collection process 100 of FIG. 2 and may require processing and interpretation similar to that detailed with reference to processes 200 and/or 300 of FIGS. 3 and 4 respectively. Information generated based on the physical fit and the simulated fit may require some degree of similarity to be comparable.

Figure 10A:
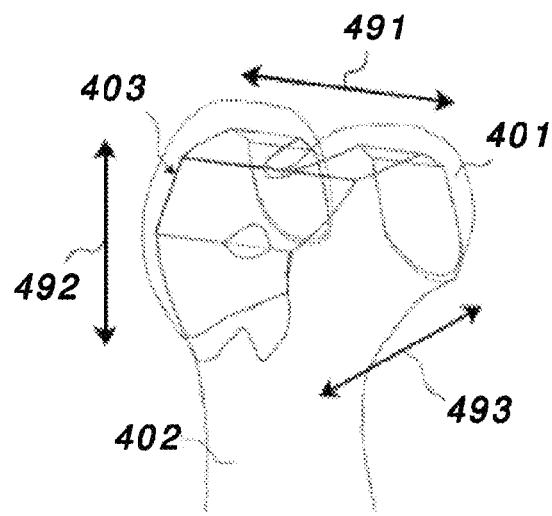
FIG. 10A illustrates generally the forms of recommended translational alterations to an existing physical connective interface that may be derived from the comparison between itself and a virtual version of equal or superior quality.
Figure 10B:
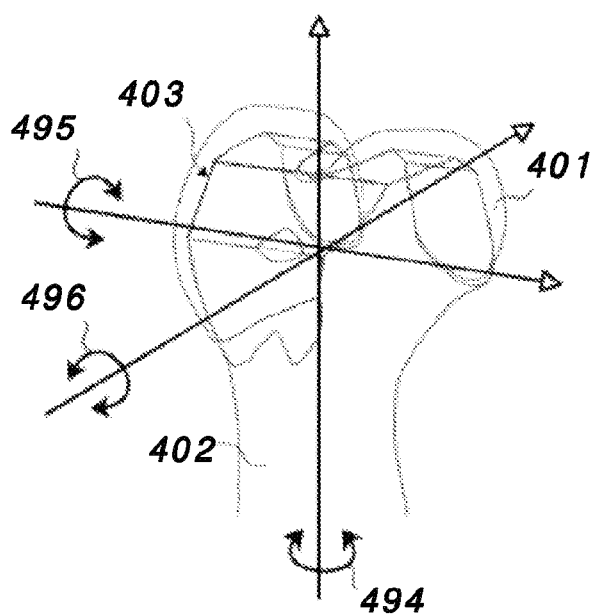
FIG. 10B illustrates generally the forms of recommended rotational alterations to an existing physical connective interface that may be derived from the comparison between itself and a virtual version of equal or superior quality.

Feedback based on the comparison may be quantitative or qualitative. Quantitative feedback may consist of directives that provide information on how much the existing implant or tissue should be adjusted to achieve a more favourable comparison. FIG. 10A demonstrates the types of directives which may be used including the movement of the implant or tissue in all spatial directions 491, 492 and 493 and FIG.

10B demonstrates the types of directives which may be used including the rotation of the implant or tissue across all rotation axes 494, 495 and 496.

Qualitative feedback may consist of recommendations or additional notes based on the insertion process. This may include an analysis of the amount of force used and if this should be increased or decreased, historical patterns or otherwise favouritism towards a particular insertion issue and if the insertion angle was suboptimal.

The insertion may be reverted when it is deemed comparatively unfavourable beyond a certain limit. In this scenario, the simulated fit, physical fit and some additional calculations, such as surface breakage or fixative displacement predictions as discussed above, will need to be repeated.

Figure 11:
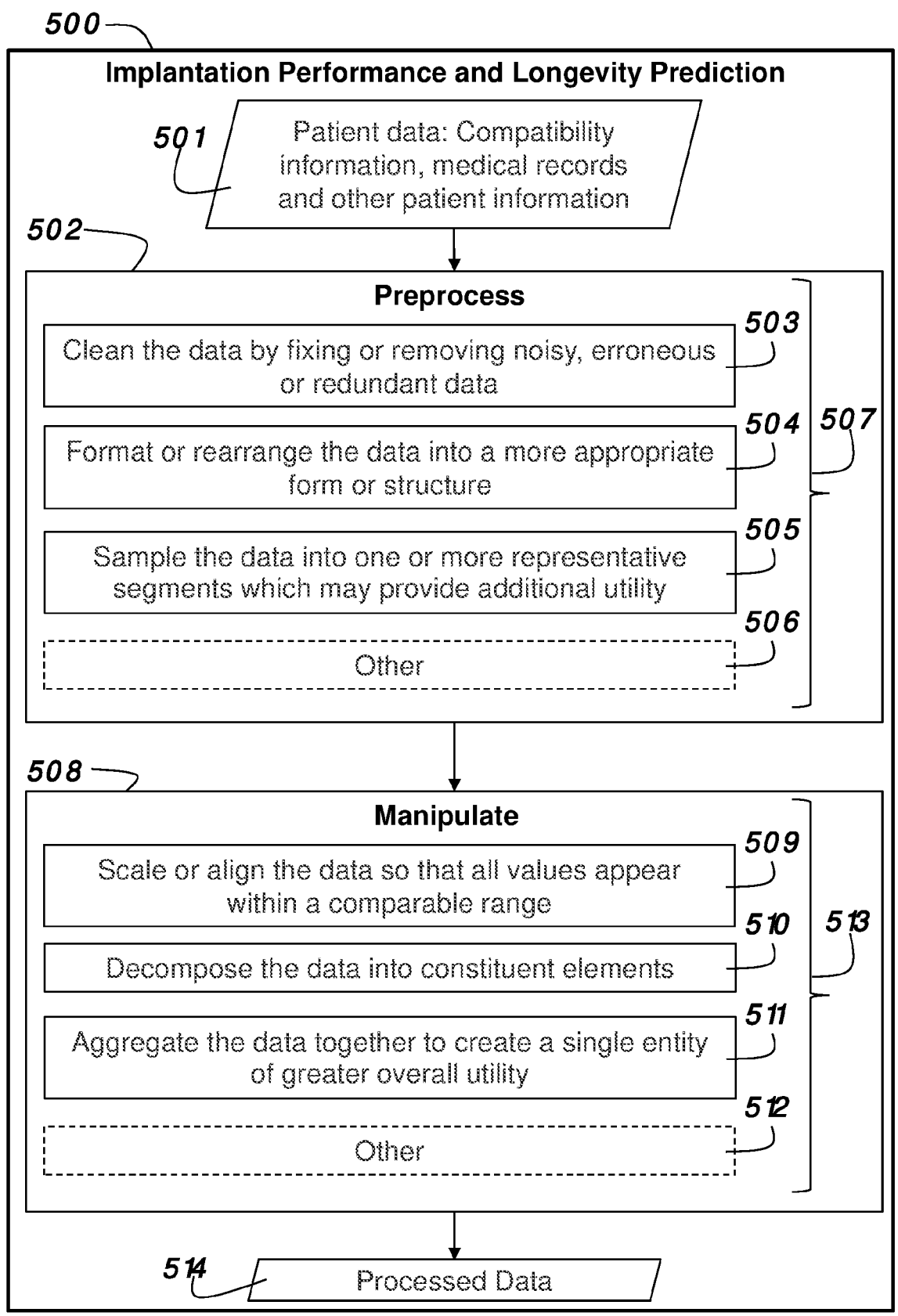
FIG. 11 is a detailed schematic flow diagram depicting the pre-processing and manipulation required to transform data into a more evaluable form for further usage within predictive algorithms and methods.

FIG. 11 is a detailed schematic diagram depicting the data processing portion of an exemplary implantation performance and longevity prediction step 500 of the implant fit analysis process 10 as depicted in FIG. 1. The processes and steps involved are very similar to those detailed in procedure 200 of FIG. 3 with the exception of the data source and the intent behind processing the data.

The data source involved is the raw compatibility information, medical records and other patient data 501 which were either generated (e.g. from suitable sensors during the procedure) or obtained from external sources. This data should contain enough information to determine how compatible its associated implant and tissue is along with the health and lifestyle details of the effected patient.

The intent behind processing the data is to best prepare the data 501 for training and execution within predictive algorithms and methods. This may involve different types of pre-processing and manipulation to transform the data into a form that produces the most benefit with respect to this usage.

Pre-processing 502 the data involves transforming it into a form of superior usability in preparation for and to produce the most utility from subsequent data manipulation 508. This data may initially be in an inappropriate form, likely used for the purpose of describing a particular connective interface 403. Since this purpose differs from the intended predictive analysis, it is possible that at least some portion of the data provided could be considered to be noisy, erroneous or redundant and may be processed as discussed above. As this could potentially introduce inconsistencies within subsequent processing. To minimise the risk of such inconsistencies affecting the results, all flawed portions or other issues existing within the data should be cleaned 503 either through removal or by being fixed as discussed above, provided that the amount of benefit produced by fixed portions outweighs the effort required to achieve them. In a particular embodiment, flawed data may be immediately removed unless a viable path to fixing them exists.

Patient data 501 may need to be rearranged and formatted 504 as part of pre-processing step 502 to increase its efficiency and make its storage more logical in relation to various predictive approaches. Its current form will likely reflect its usage in describing the interface 403 between the implant 401 and associated tissue 402 and may be presented in manner to increase its efficiency in doing so, which is likely suboptimal for predictive analysis.

In particular embodiments, and specifically for the intended predictive approaches, rearrangement step 504 consists of grouping together data which may have established similarities or other relations. This makes accessing or searching for related data or data which cleanly represents a particular aspect or series of aspects easier and more efficient. Formatting will consist of structuring these different groupings in ways that allow different sets of data to be manipulated and analysed simultaneously and subsequently. This will make traversal from one set of data to another related set of data relatively simplistic and computationally inexpensive. Other embodiments will have differing approaches to formatting and arrangement depending on the type of manipulation and subsequent predictive approaches intended for the data.

Patient data 501 may be sampled 505 as part of pre-processing step 502 to create different portions which may provide additional utility as opposed to operating based on the data as a whole. Sampling 505 consists of reducing the data pool into one that is more advantageous towards a specific type of usage, such as the data as a whole being reduced to only parts that may be deemed as representative.

In particular embodiments, and specifically for the intended predictive approaches, the data 501 is initially sampled 505 to create a single data pool that is more representative than the data as a whole. This is to say that the utility provided by this representative data pool should be equal to or superior than it was originally. This representative pool will then be split into three different segments. The first and largest segment, known as the training set, will be used for training the predictive algorithms and methods. A second, smaller, segment, known as the test set, will be used for testing trained predictive approaches. The third segment, again smaller than the training set, known as the validation set, will be used for validating the results of trained predictive approaches that have produced favourable accuracy against the test set.

Other embodiments will likely use a similar sampling approach as is consistent with predictive approaches, although additional customisations may be made depending on their specifics.

Manipulating 508 the patient data 501 involves transforming it into a form of superior evaluability in preparation for and to produce the most utility from subsequent predictive algorithms or methods 513. This data may initially be in a form wherein each value exists based on how it was expressed originally. Since each expression will likely be different across the data, achieving an appropriate level of comparability between the different sets may not be viable or may be done so to suboptimal degrees. By scaling or aligning these values to a common point 509, comparability between the different sets increases.

In the preferred particular embodiments, and specifically for the intended predictive approaches, all values existing within data sets that may be deemed comparable and which have direct or similarly equivalent initial expressions should be scaled 509. This is because some types of predictive analysis generally work better when all data exists within some known range. It also makes handling the data and distinguishing it easier, especially when presenting the data, should the need arise. Other embodiments will likely use similar scaling techniques which will again be based on their intended predictive algorithms or methods.

Patient data 501 may be reduced, split or decomposed 510 into their constituent elements as part of data manipulation in accordance with requirements. These resulting individual elements compose the data and can be used to identify which existing features may be more beneficial or representative in comparison to others. This is important for predictive analysis as these types of features generally make good indicators, which may increase their utility greatly.

In particular embodiments, and specifically for the intended predictive approaches, data is decomposed 510 into constituent elements if it can be seen that the individual elements or otherwise features make a considerable contribution in determining the overall description of the data as a whole.

Provided data 501 and the constituent elements derived from it may be aggregated 511 together into a single entity as part of data manipulation. The aggregated entity should provide more utility in comparison to the individual elements or data which were used to create it, although this may not be the case if the decision was made from a storage or computational perspective.

Aggregation approaches are typically dependent on the type and expression of the data or constituent elements involved. Elements may need to share a degree of similarity or equivalency to be considered for aggregation.

In particular embodiments, and specifically for the intended predictive approaches, elements should be aggregated 511 together if additional utility will be produced. This means that if an aggregated entity indicates the properties of a set of data better in comparison to the individual elements, then the aggregation should be maintained.

The final processed data 514 is produced after the provided data 501 has been pre-processed 502 and manipulated 508 in accordance with requirements. Other pre-processing approaches 506 and manipulation approaches 512 may exist externally to those explicitly outlined herein and do not necessarily have to be performed in the presented order or at all 511. The determination and ordering of approaches is entirely dependent on the data available and the intended application.

Other pre-processing approaches 506 and manipulation approaches 512 may also be utilised as appropriate as would be appreciated by the skilled addressee in addition to those mentioned above. The ordering and existence of these pre-processing approaches 507 and manipulation approaches 513 may not necessarily reflect the ordering and existence of the approaches as depicted in FIG. 11.

Figure 12:
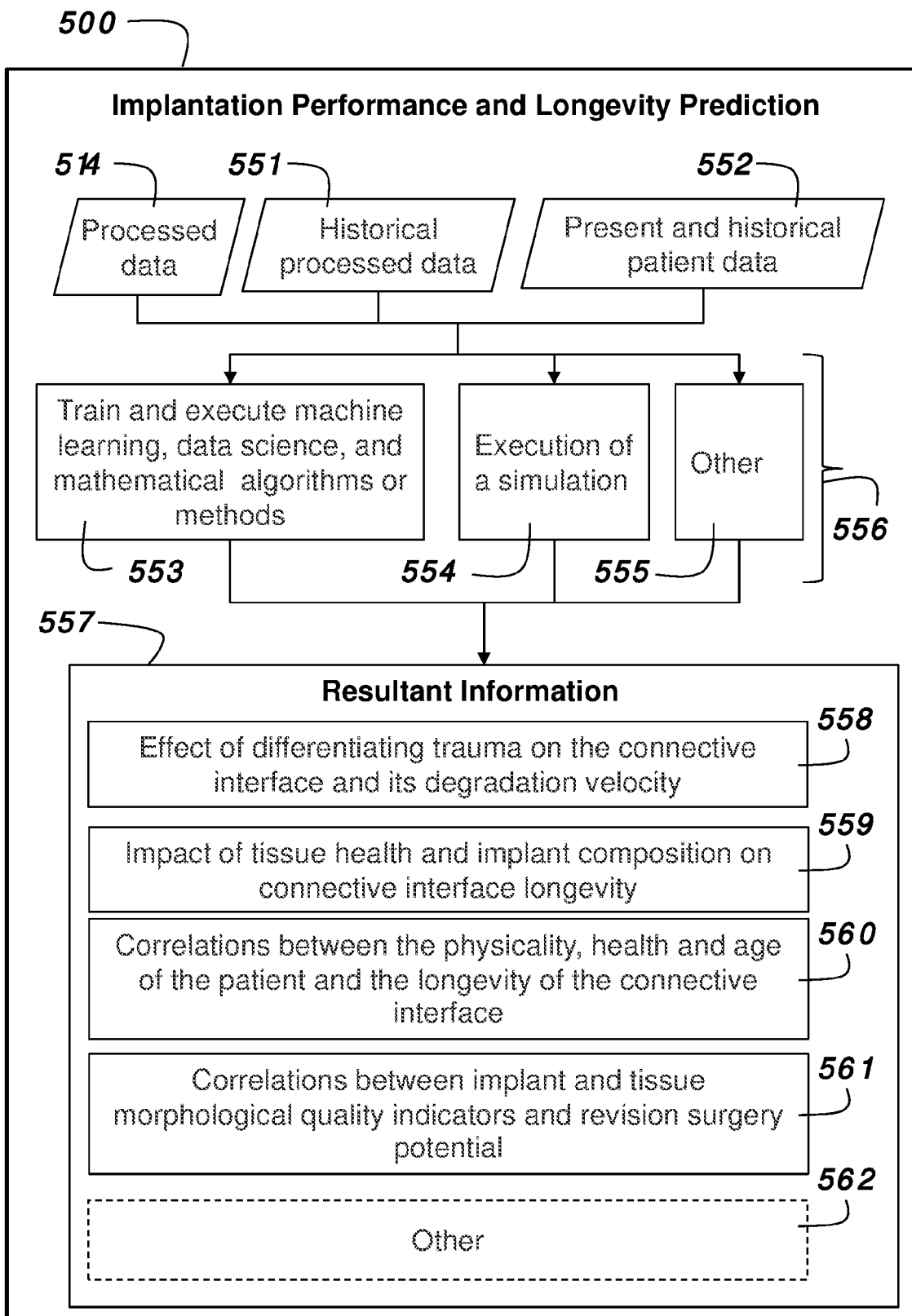
FIG. 12 is a detailed schematic flow diagram depicting the types of predictive algorithms and methods capable of producing information and properties relating to the longevity and performance of a specific connective interface based on existing processed data.

FIG. 12 shows a detailed schematic diagram depicting the information prediction portion of an exemplary implantation performance and longevity prediction step 500 of the implant fit analysis process 10 as depicted in FIG. 1. This involves using three different data sources within a series of different predictive approaches to generate information and values which may provide insight into how long an implantation will last and the cause, if any, of its degradation.

The first data source is the compatibility information, medical records and other patient data 514 which has been recently processed to produce additional utility during predictive analysis as detailed in FIG. 11. The second data source is the same except that it contains additional historical processed data 551 that has been generated prior. These sources will be used as derivable data where indicators and other mapping mechanisms may be found.

The third data source, which contains a specific set of values corresponding to each value within the second data source 551, is the historical data of actual implantation performance and longevity measures provided by previous patients 552. This is used as the ground truth and is what may be predicted.

Predictions may be generated based on the first data source 514 by training and executing 553 different forms of machine learning, data science and mathematical algorithms or methods. In particular embodiments, this will mainly consist of different supervised approaches. These types of approaches generally operate in two different phases comprising the training phase and the execution phase.

The training phase involves the second and third data sources 551 and 552 wherein each set of data in the second data source 551 maps to a specific set of values in the second 552. It consists of identifying indicators within each set of data that are either partially or majorly responsible for this mapping such that if another set of data contained these same indicators, it would be likely that it would also have the same or similar corresponding values. This will continue until a mapping structure has been developed that will map parsed indicators to values that they most commonly refer to.

The execution phase involves only the first data source 514 which has no known corresponding values. It initially consists of identifying the same indicators found during the training phase within each set of data in this source. These indicators are then given to the previously created mapping structure to identify the values that they correspond to. These values are then defined as the values which the initial set of data may correspond to.

This training phase is often performed using different segments of data as opposed to the data as a whole which may include training, testing and validation segments, where the data and corresponding values are known for each. It will initially begin by generating a mapping structure corresponding to only the training segment. The data within the test segment will then be ran through this structure, with the values it returns being compared to the actual known values of the segment. This will provide a measure of accuracy depending on how close the returned values are to the actual ones. If this accuracy is satisfactory (somewhere between 95-100% based on the particular embodiment) then it is tested again using the validation segment. This is to simulate its performance on real world data as although it has seen the training and test segments previously, the validation segment will remain unknown to it. This ensures that the mapping structure will perform well on all data as opposed to only the test segment, a phenomenon known as overfitting.

Supervised algorithms or methods differ greatly in their complexity as well as their predictive power and using various types of them concurrently may produce beneficial results in addition to a point of comparison. These algorithms or methods may include linear and polynomial regression, logistic regression, naïve bayesian networks, bayesian networks, support vector machines, decision trees, random forests, k-nearest neighbour classifiers and neural networks alternatively including other algorithms or methods as would be appreciated by the skilled addressee.

Other embodiments may use different predictive approaches, including unsupervised, semi-supervised and reinforcement approaches as would be appreciated by the skilled addressee. Unsupervised and semi-supervised algorithms or methods are provided a data set and are made to extract meaning from it without any or with little direction as to what it is that they are looking for. This allows unknown information or connections existing within the data to be found which may provide additional utility depending on what they are and their consistency in other data sets.

Reinforcement algorithms or methods may attempt to run a series of calculations with the goal of producing a particular value. They are provided positive or negative stimulus depending on the accuracy of this value in comparison to what is should have been. When provided positive stimulus, they will continue performing the same calculations that they have done and may perform additional ones which are similar to these. When provided negative stimulus they may stop performing their current calculations and try some that are different to varying degrees. A degree of randomness is typically added to these algorithms to give them a starting point, which means that they may require more execution cycles to reach a satisfactory result in comparison to the prior predictive analysis approaches.

Predictions may be generated based on processed data 514 by running a simulation that involves the different types of scenarios, events and conditions that may affect the implantation 553. These types of instances will likely be simulated mathematically with probabilistic measures added to account for situations that are not currently determinative.

In particular embodiments, the simulation will be designed around different types of implantation degradation and the scenario in which these may take form. It will be provided two main sources of data.

The first source 514 will be processed data that contains various information relating to the quality of the implantation procedure. This will be used to discern the types of issues that may be most prevalent or that the implant and associated tissue will be vulnerable to.

The second source 552 will be information relating to the lifestyle and other aspects of a patient which may include their level of activity and the average amount of trauma that their implantation may sustain as a result. This information will indicate the rate and degree of exacerbation that any issues may undergo, and the probability of physical trauma causing them.

Currently the simulation has been referred to as singular but this may not be the case if additional benefit can be found by dividing it into individual simulations that each have their own purpose or predictive goal. Considering the complexity that is usually involved, division may be advantageous at least from a development and production point of view.

Other embodiments may utilise different simulations depending on their context and application. This would likely be dependent on the form of implantation as procedures occurring within the human body would be affected differently depending on what tissue or body part they may be replacing or reinforcing.

Predictions generated will be used to provide insight into information relating to the performance and longevity of the implantation procedure 556. These types of information typically revolve around either the impact of certain variables on the implantation 557-558, or the correlation between some variables and the state of the implantation 559-560. In particular embodiments, they will be mainly based on orthopaedic indicators that define when issues may arise with a particular implantation. This will allow for appointments to be booked in advance and certain precautions to be taken intraoperatively to result in a more favourable outcome.

The lifestyle of the patient in terms of their activity level indicates how much trauma the implant will typically endure. The effect of this trauma and how it can be exacerbated over a period of time may be predicted 558 by comparing this activity level, or any particularly high-impact events, with the rate of degradation determined based on patient input.

The composition of the implant and the health of the tissue will be known to a certain degree prior to the implantation procedure. Issues that exist between these two sets of information may be predicted 559 by comparing them together with respect to the lifetime of the implant and when the patients may require revision surgery.

The physicality, health and age of the patient can be assumed to have a strong correlation 560 to the longevity of the implantation. The types of situations and trauma that the implantation would likely be vulnerable to may possibly be determined through this correlation. The point at which revision is deemed to be necessary may be predicted based on this information and the historical data of similar patients.

The morphology of the tissue and implant 561 determines the quality of the associated fit or connective interface that may exist between them. If this connective interface begins to degrade, then the morphology will likely be an insightful indicator as to the possible reasons for the degradation over time, especially when used in conjunction with predictions made relating to the health and composition of the implant and tissue 558. By comparing the morphology and therefore indicators relating to the quality of the connective interface against the point at which revision surgery was deemed necessary, it may be possible to predict when this point will occur.

Other predictive approaches and resultant information may exist external to those explicitly outlined herein 561. Predictive approaches may not necessarily only be executed singularly, they may also be executed concurrently and subsequently if reason exists to do so 556.

Figure 13:
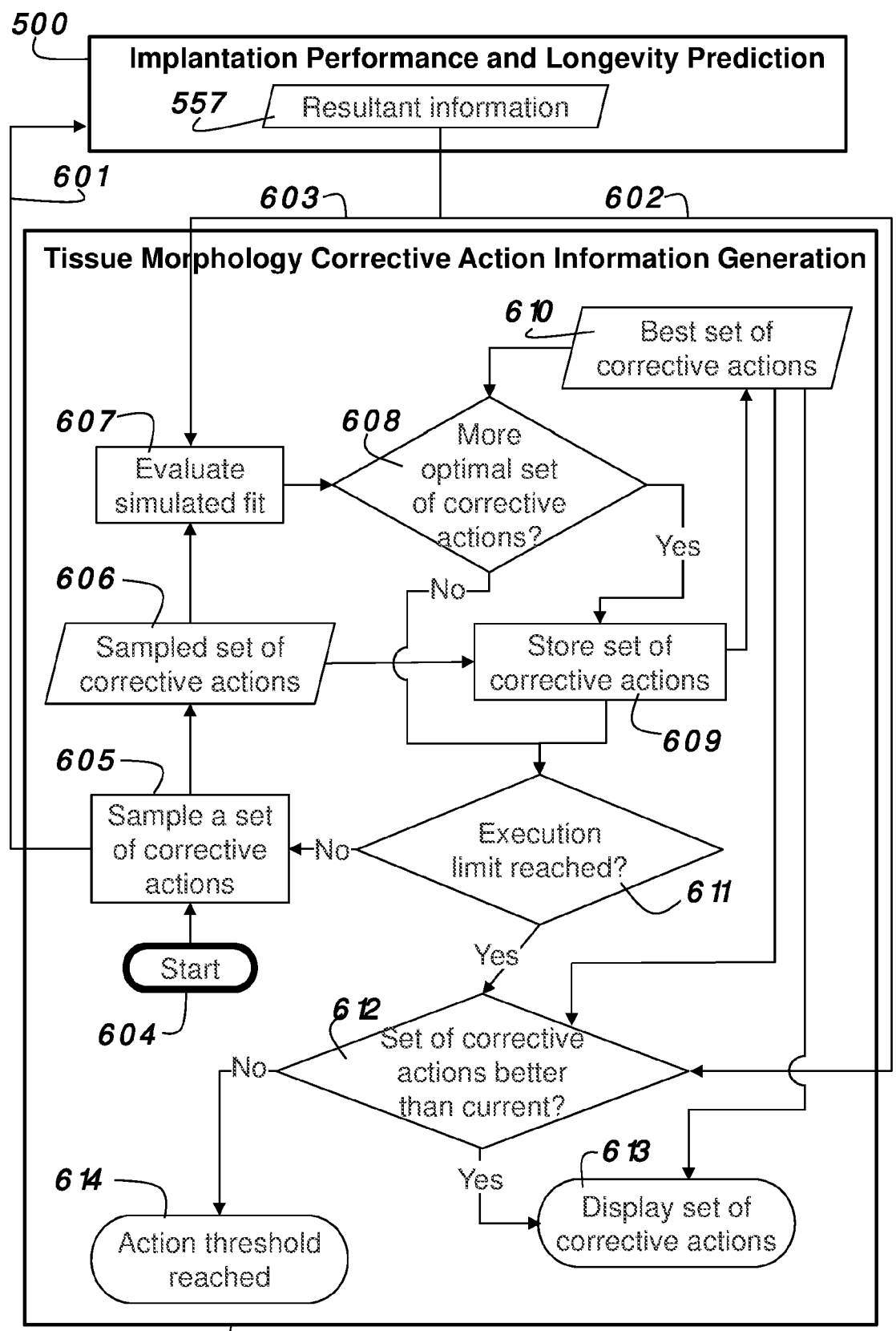
FIG. 13 is a detailed schematic flow diagram depicting the process by which a set of corrective actions to alter the tissue morphology is determined.

FIG. 13 shows a detailed schematic diagram depicting the generation of a set of tissue morphology corrective actions for the surgeon to consider implementing.

The start 604 of the process begins with an initial sampling 605 of a set of corrective actions that is ideal for changing the tissue morphology to the best mechanical alignment.

The resulting sampled set of corrective actions 606 for an ideal mechanical alignment may not be possible to implement for a variety of reasons which will be detailed herein.

Firstly, there may not be enough existing tissue to form a secure fit that would result in the best implantation performance and longevity prediction 500.

Additionally, the accuracy of the surgical resection tools being used may be below a threshold that would allow for the precise application of the set of corrective actions. For instance, if the ideal tissue morphology is a thin slice on a slight angle it may be beyond the capability of the surgeon using the tools available.

As discussed above, the estimated resulting tissue morphology is delivered to the implantation performance and longevity prediction 500 to be simulated to provide resultant information 557 that can be used to compare against other simulated sets of actions and the existing state of the tissue.

The resultant information 557 for the simulated resulting tissue morphology is evaluated 607 to determine if the set of actions are desirable, as detailed above, and if so to calculate one or more numerical quantifications to use as comparator values.

Should the resultant information 557 is compared 608 against the best set of corrective actions 610, if any, simulated so far in the process. If the resultant information 557 is a more optimal set of corrective actions as compared, the sampled set of corrective actions 606 are stored 609 and replace the best set of corrective actions 610.

The process will then consider 611 if the current execution limit 611 has been reached. This is a limit of some type of scarce resource, for example: computational time, real time, energy, storage space, or cooling capacity.

If there are resources available to continue to seek out better sets of corrective actions, a relaxed set of corrective actions 605 will be sampled.

If the resources are exhausted, the best set of corrective actions 610 is compared 612 against the current morphology's resultant information 557.

If the best set of corrective actions 610 is superior by a pre-determined threshold value then it is displayed to the surgeon 613 for their consideration to implement. This may in turn result in another implantation performance and longevity prediction based on the tissue state and morphology after the surgeon has performed the set of corrective actions.

If the best set of corrective actions 610 is not superior by a pre-determined threshold value then the process will alert the operator that the action threshold has been reached 614, indicating that further substantial improvement is unlikely to be achieved.

The features presented herein may be performed electronically through any capable system or machine that can complete them within any restrictions applied by their particular application. This may be performed online, offline or in a capacity that relies on some combination of the two.

Data extracted or generated as a result of the features presented herein may be stored electronically which can be done offline, online, or through some combination of the two. This may be accessed immediately or in a delayed time frame for retrieval, processing and any other form of usage. All types of data may be stored but some may only be maintained intermittently.

It should be understood that the features presented herein and the different processes that they contain do not necessarily need to be performed in the described order nor do they require a specific environment or situation. Their ordering, nature, preparation and execution may be dependent on numerous circumstances as is typically the case with medically applicable inventions or methods. One such circumstance may be patient state and morphology which may require additional processes or customisations to concur with any specific issues or restrictions as is common in medical practises such as orthopaedics.

It will be appreciated by those skilled in the art that variations and modifications to the invention described herein will be apparent without departing from the spirit and scope thereof. The variations and modifications as would be apparent to persons skilled in the art are deemed to fall within the broad scope and ambit of the invention as herein set forth.

Future patent applications may be filed in Australia or overseas on the basis of, or claiming priority from, the present application. It is to be understood that the following provisional claims are provided by way of example only and are not intended to limit the scope of what may be claimed in any such future application. Features may be added to or omitted from the provisional claims at a later date so as to further define or re-define the invention or inventions.

Figure 14:
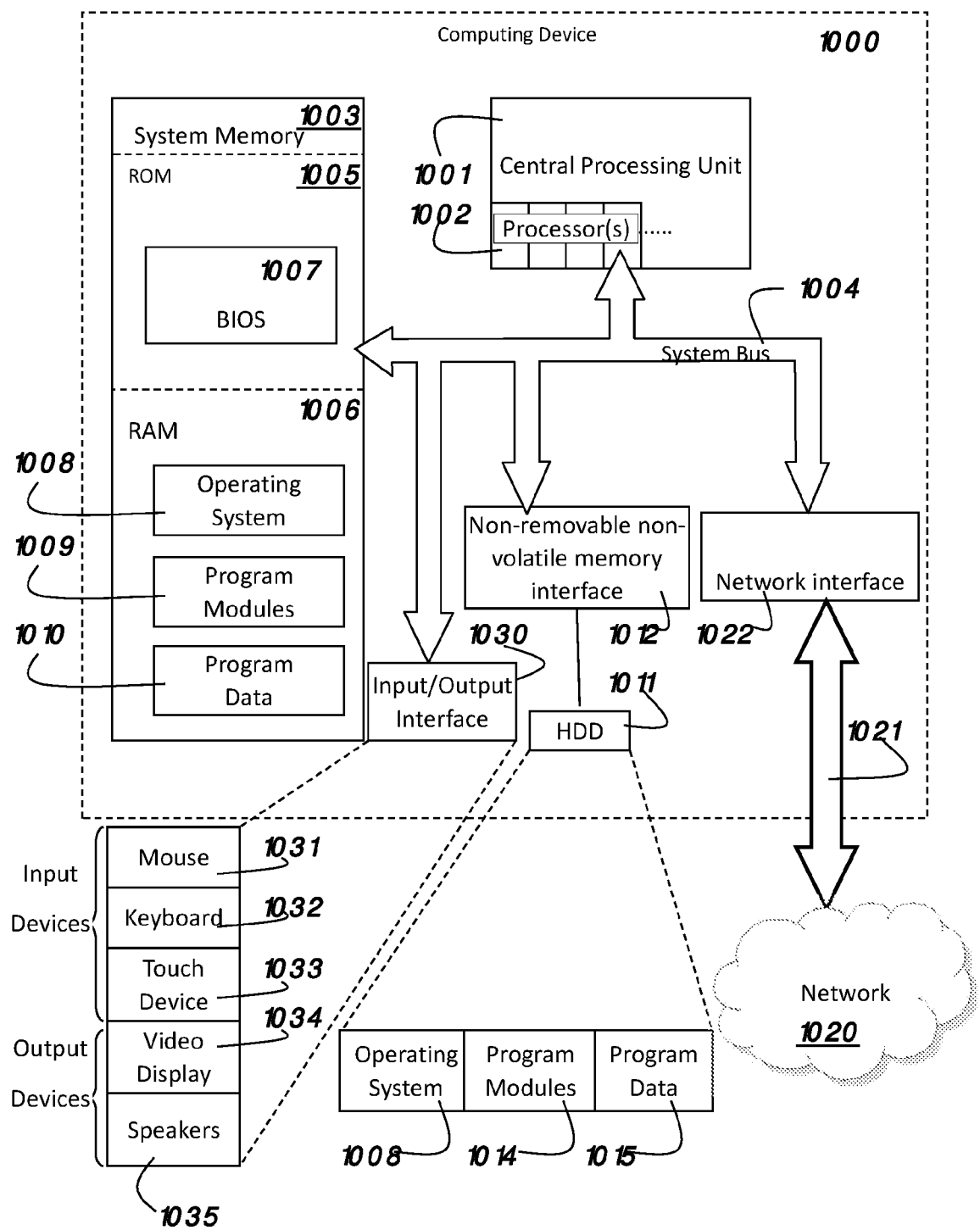
FIG. 14 shows a computing device on which the various embodiments described herein may be implemented in accordance with an embodiment of the present invention.

The methods of 10, 100, 200, 300, 400, 500, and 600 (and associated sub methods described herein) as depicted in FIGS. 1 to 4 and 11 to 13 may be implemented using a computing device/computer system 1000, such as that shown in FIG. 14 wherein the processes of FIGS. 1 to 13 may be implemented as software, such as one or more application programs executable within the computing device 1000. In particular, the steps of methods 10, 100, 200, 300, 400, 500, and 600 are affected by instructions in the software that are carried out within the computer system 1000. The instructions may be formed as one or more code modules, each for performing one or more particular tasks. The software may also be divided into two separate parts, in which a first part and the corresponding code modules performs the described methods and a second part and the corresponding code modules manage a user interface between the first part and the user. The software may be stored in a computer readable medium, including the storage devices described below, for example. The software is loaded into the computer system 1000 from the computer readable medium, and then executed by the computer system 1000. A computer readable medium having such software or computer program recorded on it is a computer program product. The use of the computer program product in the computer system 1000 preferably effects an advantageous apparatus for quality analysis of the implantation process and the predicted longevity of the orthopaedic implant within an intraoperative environment.

With reference to FIG. 14, an exemplary computing device 1000 is illustrated. The exemplary computing device 1000 can include, but is not limited to, one or more central processing units (CPUs) 1001 comprising one or more processors 1002, a system memory 1003, and a system bus 1004 that couples various system components including the system memory 1003 to the processing unit 1001. The system bus 1004 may be any of several types of bus structures including a memory bus or memory controller, a peripheral bus, and a local bus using any of a variety of bus architectures.

The computing device 1000 also typically includes computer readable media, which can include any available media that can be accessed by computing device 1000 and includes both volatile and non-volatile media and removable and non-removable media. By way of example, and not limitation, computer readable media may comprise computer storage media and communication media. Computer storage media includes media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the computing device 1000. Communication media typically embodies computer readable instructions, data structures, program modules or other data in a modulated data signal such as a carrier wave or other transport mechanism and includes any information delivery media. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 1003 includes computer storage media in the form of volatile and/or non-volatile memory such as read only memory (ROM) 1005 and random access memory (RAM) 1006. A basic input/output system 1007 (BIOS), containing the basic routines that help to transfer information between elements within computing device 1000, such as during start-up, is typically stored in ROM 1005. RAM 1006—typically contains data and/or program modules that are immediately accessible to and/or presently being operated on by processing unit 1001. By way of example, and not limitation, FIG. 14 illustrates an operating system 1008, other program modules 1009, and program data 1010.

The computing device 1000 may also include other removable/non-removable, volatile/non-volatile computer storage media. By way of example only, FIG. 14 illustrates a hard disk drive 1011 that reads from or writes to non-removable, non-volatile magnetic media. Other removable/ non-removable, volatile/non-volatile computer storage media that can be used with the exemplary computing device include, but are not limited to, magnetic tape cassettes, flash memory cards, digital versatile disks, digital video tape, solid state RAM, solid state ROM, and the like. The hard disk drive 1011 is typically connected to the system bus 1004 through a non-removable memory interface such as interface 1012.

The drives and their associated computer storage media discussed above and illustrated in FIG. 14, provide storage of computer readable instructions, data structures, program modules and other data for the computing device 1000. In FIG. 14, for example, hard disk drive 1011 is illustrated as storing an operating system 10YY, other program modules 1014, and program data 1015. Note that these components can either be the same as or different from operating system 1008, other program modules 1009 and program data 1010. Operating system 3013, other program modules 1014 and program data 1015 are given different numbers hereto illustrate that, at a minimum, they are different copies.

The computing device also includes one or more input/output (I/O) interfaces 1030 connected to the system bus 1004 including an audio-video interface that couples to output devices including one or more of a video display 1034 and loudspeakers 1035. Input/output interface(s) 1030 also couple(s) to one or more input devices including, for example a mouse 1031, keyboard 1032 or touch sensitive device 1033 such as for example a smartphone or tablet device.

Of relevance to the descriptions below, the computing device 1000 may operate in a networked environment using logical connections to one or more remote computers. For simplicity of illustration, the computing device 1000 is shown in FIG. 14 to be connected to a network 1020 that is not limited to any particular network or networking protocols, but which may include, for example Ethernet, Bluetooth or IEEE 802. X wireless protocols. The logical connection depicted in FIG. 14 is a general network connection 1021 that can be a local area network (LAN), a wide area network (WAN) or other network, for example, the internet. The computing device 1000 is connected to the general network connection 1021 through a network interface or adapter 1022 which is, in turn, connected to the system bus 1004. In a networked environment, program modules depicted relative to the computing device 1000, or portions or peripherals thereof, may be stored in the memory of one or more other computing devices that are communicatively coupled to the computing device 1000 through the general network connection 1021. It will be appreciated that the network connections shown are exemplary and other means of establishing a communications link between computing devices may be used.

Interpretation
Bus

In the context of this document, the term "bus" and its derivatives, while being described in a preferred embodiment as being a communication bus subsystem for interconnecting various devices including by way of parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like, should be construed broadly herein as any system for communicating data.

In Accordance With

As described herein, 'in accordance with' may also mean 'as a function of' and is not necessarily limited to the integers specified in relation thereto.

Composite Items

As described herein, 'a computer implemented method' should not necessarily be inferred as being performed by a single computing device such that the steps of the method may be performed by more than one cooperating computing devices.

Similarly objects as used herein such as 'web server', 'server', 'client computing device', 'computer readable medium' and the like should not necessarily be construed as being a single object, and may be implemented as a two or more objects in cooperation, such as, for example, a web server being construed as two or more web servers in a server farm cooperating to achieve a desired goal or a computer readable medium being distributed in a composite manner, such as program code being provided on a compact disk activatable by a license key downloadable from a computer network.

Database

In the context of this document, the terms "data source" and "database" are interchangeable and derivatives of these terms may be used to describe a single database, a set of databases, a system of databases or the like. The system of databases may comprise a set of databases wherein the set of databases may be stored on a single implementation or span across multiple implementations. The term "database" is also not limited to refer to a certain database format rather may refer to any database format. For example, database formats may include MySQL, MySQLi, XML or the like.

Processes

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor

In a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory subsystem including main RAM and/or a static RAM, and/or ROM.

Computer-Readable Medium

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Implementation

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying out a Method or Function

Furthermore, some of the embodiments are described herein as a method or combination of elements of a method that can be implemented by a processor or a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment/arrangement, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment/arrangement of this invention.

Furthermore, while some embodiments described herein include some but not other features included in other embodiments, combinations of features of different embodiments are meant to be within the scope of the invention, and form different embodiments/arrangements, as would be understood by those in the art. For example, in the following claims, any of the claimed embodiments can be used in any combination.

Additional Embodiments

Thus, one embodiment of each of the methods described herein is in the form of a computer-readable carrier medium carrying a set of instructions, e.g. a computer program that are for execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the embodiments of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", and the like are used as words of convenience to provide reference points and are not to be construed as limiting terms.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

Scope of Invention

Thus, while there has been described what are believed to be the preferred arrangements of the invention, those skilled in the art will recognize that other and further modifications may be made thereto without departing from the spirit of the invention, and it is intended to claim all such changes and modifications as fall within the scope of the invention. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

Industrial Applicability

It is apparent from the above, that the arrangements described are applicable to the mobile device industries, specifically for methods and systems for distributing digital media via mobile devices.

It will be appreciated that the methods/apparatus/devices/systems described/illustrated above at least substantially provide a methods and systems for quality analysis of the implantation process and the predicted longevity of the orthopaedic implant within an intraoperative environment.

The systems and methods described herein, and/or shown in the drawings, are presented by way of example only and are not limiting as to the scope of the invention. Unless otherwise specifically stated, individual aspects and components of the systems and methods may be modified, or may have been substituted therefore known equivalents, or as yet unknown substitutes such as may be developed in the future or such as may be found to be acceptable substitutes in the future. The systems and methods may also be modified for a variety of applications while remaining within the scope and spirit of the claimed invention, since the range of potential applications is great, and since it is intended that the present systems and methods be adaptable to many such variations.

The invention claimed is:

1. A method for intraoperative implant fit analysis and longevity prediction for a prosthetic implant to be integrated with physiological tissue of a patient, comprising:
   during a surgical procedure, collecting data by one or more computing devices via a plurality of sensors situated in proximity to a tissue and an implant and a plurality of data sources, wherein the plurality of sensors are included within a surgical environment in which the surgical procedure is occurring;
   modifying, during the surgical procedure and by the one or more computing devices, the collected data to remove data dimensions;
   determining, during the surgical procedure and by the one or more computing devices, a tissue state, a tissue morphology, an implant state, and an implant morphology based on the modified collected data;
   generating, during the surgical procedure and by the one or more computing devices, compatibility information that describes a simulated fit between the tissue and the implant based on the tissue state, the tissue morphology, the implant state, and the implant morphology;
   processing, during the surgical procedure and by the one or more computing devices, the compatibility information into a form adapted for evaluation against a pre-determined comparator;
   generating and displaying, during the surgical procedure and by the one or more computing devices and via a display device, a visualization that depicts the simulated fit, wherein the visualization is generated based on the data that is collected via the plurality of sensors;
   generating and providing, by the one or more computing devices, a set of corrective actions for alteration of the tissue state and the tissue morphology for improved postoperative implant performance and longevity;
   receiving, during the surgical procedure and by the one or more computing devices and via the plurality of sensors, additional data describing a physical fit between the tissue and the implant;
   comparing, during the surgical procedure and by the one or more computing devices, the simulated fit depicted by the visualization with i) the physical fit and ii) the set of corrective actions;
   in response to the comparing the simulated fit during the surgical procedure and by the one or more computing devices, modifying the set of corrective actions; and
   configuring, during the surgical procedure and by the one or more computing devices, the display device to provide the modified set of corrective actions.

2. The method of claim 1, wherein the tissue comprises biological tissue.

3. The method of claim 1, wherein the prosthetic implant comprises a knee prosthetic, or a hip prosthetic.

4. The method of claim 1, wherein the prosthetic implant comprises one or more features comprising threading or patterns on one or more surfaces to encourage at least one of osseointegration or increase of a rigidity of a fixation to the tissue.

5. The method of claim 1 wherein the sensors comprise at least one sensor that is individually configured to monitor, sense, collect, and provide data based on various properties, characteristics, occurrences or measures of a subject.

6. The method of claim 5, wherein the subject comprises one or more of the tissue, the implant, a connective interface between the tissue and the implant, a surrounding environment, or a result of an action or interaction.

7. The method of claim 1, wherein at least one of the sensors requires external involvement comprising at least one of a change to its position, angle, vicinity, proximity, configuration, lighting, or timing.

8. The method of claim 1, wherein the tissue state comprises at least one of composition, hydration, density, necrosis, colouration, reflectance, or temperature.

9. The method of claim 1, wherein the implant state comprises at least one of composition, deterioration, density, or particle dissolution.

10. The method of claim 1, wherein each of the tissue morphology and the implant morphology comprises one or more of shape, flatness, parallelism, roughness, waviness, peak distribution, porosity, or rigidity.

11. The method of claim 1, further comprising processing, by the one or more computing, the collected data prior to determining the tissue state, the implant state, the tissue morphology and the implant morphology, wherein processing the collected data comprises at least one of:
   removing any noise, erroneous or redundant data from the collected data;
   formatting the collected data, flattening the collected data, or extracting the collected data from storage;

sampling the collected data;
scaling or aligning the collected data so that its values are within a comparable range;
decomposing or deconvoluting the collected data so that representative or specific features or portions of the collected data can be split into constituent elements; or
aggregating the collected data so that individual features, constituent elements, sections or portions of the collected data may be combined into a single entity.

12. The method of claim 11, wherein determining the tissue state, the tissue morphology, the implant state, and the tissue morphology comprises interpretation of the processed collected data.

13. The method of claim 12, wherein the interpretation of the processed collected data comprises execution of machine learning, data science or mathematical algorithms or methods.

14. The method of claim 12, wherein the interpretation of the processed collected data is performed by at least one of a sensor controller or a bridging device.

15. The method of claim 12, wherein the interpretation of the processed collected data is based on observations or tacit conclusions provided by verified personnel.

16. The method of claim 1, wherein generating the compatibility information is based on interpreted data from the tissue comprising a receiving surface, an associated implant comprising an engaging surface, and an interface between the receiving surface and the engaging surface and comprises the steps of:
generating a degree of compatibility of the interface with either or both of the receiving surface and the engaging surface;
analysing an impact of implant insertion or fixation;
evaluating the implant fit; and
predicting the longevity and performance of the implant.

17. The method of claim 16, wherein generating the degree of compatibility comprises comparing the tissue state and the implant state and comparing the tissue morphology and the implant morphology.

18. The method of claim 17, wherein comparing the tissue state and the implant state comprises gauging compatibility of the tissue state and the implant state.

19. The method of claim 18, wherein gauging the compatibility of the tissue state and the implant state comprises checking health of the tissue to measure fixation potential and survivability.

20. The method of claim 17, wherein comparing the tissue morphology and the implant morphology comprises gauging compatibility of the tissue morphology and the implant morphology.

21. The method of claim 20, wherein gauging the compatibility of the tissue morphology and the implant morphology comprises determining if a shape and form of the tissue will enable the implant to be inserted.

22. The method of claim 20, wherein gauging the compatibility of the tissue morphology and the implant morphology comprises determining a degree of contact that the implant will make against the tissue when inserted.

23. The method of claim 20, wherein gauging the compatibility of the tissue morphology and the implant morphology comprises determining a degree to which the receiving surface of the tissue populates a threading of the implant and how comparable a distribution pattern of the tissue within the threading of the implant is in comparison.

24. The method of claim 16, wherein placement of the implant onto the tissue is defined by at least one of a degree of contact between the tissue and the implant, a population and distribution pattern of the tissue within a threading of the implant, or a stress distribution on the implant.

25. The method of claim 16, wherein a quality of the implant fit is influenced by the implant state, the implant morphology, the tissue state, the tissue morphology, a situation, an environment, intended usage scenarios, and stress that the implant will endure.

26. The method of claim 1, wherein the implant performance and longevity comprises quantitative measures of time and qualitative measures relating to an ease of performing certain tasks by the patient.

27. The method of claim 1, wherein the pre-determined comparator comprises a set of comparison information data in a comparable form.

28. The method of claim 1, further comprising receiving postoperative results from the patient after a duration of time has occurred.

29. The method of claim 1, further comprising training a machine learning model to provide performance predictions.

30. A system for supporting a surgical biological implantation procedure for integration of a prosthetic device with a patient's tissue comprising:
one or more sensors for sensing characteristics of a morphology of the patient's tissue to collect at least state data and morphology data to generate collected data during a surgical procedure, wherein the one or more sensors are included within a surgical environment in which the surgical procedure is occurring; and
one or more processors adapted for:
pre-processing of the collected data to generate processed data during the surgical procedure, said processed data having a form suitable for interpretation, wherein the pre-processing includes modifying the collected data to remove data dimensions;
interpreting, during the surgical procedure, the processed data for extraction of a data representation of structure of the patient's tissue and a data representation of the prosthetic device;
determining, during the surgical procedure, compatibility data that describes a simulated fit between the data representation of the structure of the patient's tissue and the data representation of the prosthetic device to determine compatibility of a connective surface of the prosthetic device with a state of a receiving surface of the patient's tissue;
predicting, during the surgical procedure, at least one of longevity or performance of the prosthetic device using the compatibility data;
generating and displaying, during the surgical procedure and via a display device, a visualization that depicts the simulated fit, wherein the visualization is generated based on the collected data that is collected via the one or more sensors;
generating, during the surgical procedure, corrective action data for modification of the receiving surface of the patient's tissue for improved prediction of the longevity or performance of the prosthetic device;
receiving, during the surgical procedure and via the one or more sensors, additional data describing a physical fit between the patient's tissue and the prosthetic device;
comparing, during the surgical procedure, the simulated fit depicted by the visualization with i) the physical fit and ii) the corrective action data;
in response to the comparing the simulated fit and during the surgical procedure, modifying the corrective action data; and configuring, during the surgical procedure, the display device to provide the modified corrective action data.

31. The system as claimed in claim 30, wherein the sensors comprise at least one of a Raman spectroscopy sensor, a spectral imaging sensor, a hyperspectral imaging sensor, an optical imaging sensor, a thermal imaging sensor, a fluorescence spectroscopy sensor, a microscopy sensor, an acoustics sensor, a 3D metrology sensor, an optical coherence tomography sensor, a position sensor, a movement sensor, or a balance sensor.

32. The system as claimed in claim 30, wherein the state data comprises attributes of at least one of a state of the patient's tissue or a state of the prosthetic device; and
   wherein the attributes comprise one or more of composition, hydration, density, necrosis, colouration, reflectance, heat consistency, deterioration, or particle dissolution.

33. The system as claimed in claim 31, wherein the morphology data comprises attributes of at least one of the morphology of the patient's tissue or a morphology of the prosthetic device; and
   wherein the attributes comprise one or more of shape, flatness, parallelism, roughness, waviness, peak distribution, porosity, or rigidity.

34. The system as claimed in claim 30, wherein said collected data further comprises historical data, wherein the historical data includes at least one of historical surgical procedure record data or historical patient data.

35. The system as claimed in claim 30, wherein said pre-processing of the collected data comprises one or more of: removing noisy, erroneous or redundant data; formatting the collected data to an appropriate data format; sampling the collected data into one or more representative segments; scaling or aligning the collected data; decomposing the collected data into constituent elements; or aggregating the collected data to create a statistically significant data structure.

36. A non-transitory computer-readable medium having instructions stored thereon, which, when executed by a processor, cause the processor to perform operations for intraoperative implant fit analysis and longevity prediction for a prosthetic implant to be integrated with physiological tissue of a patient, said operations comprising:
   during a surgical procedure, collecting data via a plurality of sensors situated in proximity to a tissue and an implant and a plurality of data sources, wherein the plurality of sensors are included within a surgical environment in which the surgical procedure is occurring;
   modifying, during the surgical procedure, the collected data to remove data dimensions;
   determining, during the surgical procedure, a tissue state, a tissue morphology, an implant state, and an implant morphology based on the collected data;
   generating, during the surgical procedure, compatibility information that describes a simulated fit between the tissue and the implant based on the tissue state, the tissue morphology, the implant state, and the implant morphology;
   processing, during the surgical procedure, the compatibility information into a form adapted for evaluation against a pre-determined comparator;
   generating and displaying, via a display device, a visualization that depicts the simulated fit, wherein the visualization is generated based on the data that is collected via the plurality of sensors;
   generating and providing, during the surgical procedure, a set of corrective actions for alteration of the tissue state and the tissue morphology for improved postoperative implant performance and longevity;
   receiving, during the surgical procedure and via the plurality of sensors, additional data describing a physical fit between the tissue and the implant;
   comparing, during the surgical procedure, the simulated fit depicted by the visualization with i) the physical fit and ii) the set of corrective actions;
   in response to the comparing the simulated fit during the surgical procedure, modifying the set of corrective actions; and
   configuring, during the surgical procedure, the display device to provide the modified set of corrective actions.

37. The non-transitory computer-readable medium as claimed in claim 36, having further instructions stored thereon to cause the processor to process the collected data prior to determining the tissue state, the implant state, the tissue morphology and the implant morphology, wherein processing the collected data comprises at least one of:
   removing any noise, erroneous or redundant data from the collected data;
   formatting the collected data, flattening the collected data, or extracting the collected data from storage;
   sampling the collected data;
   scaling or aligning the collected data so that its values are within a comparable range;
   decomposing or deconvoluting the collected data so that representative or specific features or portions of the collected data can be split into constituent elements; or
   aggregating the collected data so that individual features, constituent elements, sections or portions of the collected data may be combined into a single entity.

38. The non-transitory computer-readable medium as claimed in claim 37, wherein determining the tissue state, the tissue morphology, the implant state, and the tissue morphology comprises interpretation of the processed collected data using a machine learning model.

39. The non-transitory computer-readable medium as claimed in claim 36, wherein generating the compatibility information is based on interpreted data from the tissue comprising a receiving surface, an associated implant comprising an engaging surface, and an interface between the receiving surface and the engaging surface and comprises the operations of:
   generating a degree of compatibility of the interface with either or both of the receiving surface and the engaging surface;
   analysing an impact of implant insertion or fixation;
   evaluating the implant fit; and
   predicting the longevity and performance of the implant.

40. The non-transitory computer-readable medium as claimed in claim 39, wherein generating the degree of compatibility comprises comparing the tissue state and the implant state and comparing the tissue morphology and the implant morphology.

41. The non-transitory computer-readable medium as claimed in claim 36, the operations further comprising training a machine learning model to provide performance predictions.

* * * * *